US010695480B2

(12) United States Patent
Roy et al.

(10) Patent No.: US 10,695,480 B2
(45) Date of Patent: Jun. 30, 2020

(54) GAS EXCHANGE COMPOSITE MEMBRANES AND METHODS OF USE THEREOF

(71) Applicant: The Regents of the University of California, Oakland, CA (US)

(72) Inventors: Shuvo Roy, San Ramon, CA (US); Torin Yeager, San Francisco, CA (US); Emily Abada, San Francisco, CA (US); Ajay S. Dharia, San Bruno, CA (US)

(73) Assignee: The Regents of the University of California, Oakland, CA (US)

( * ) Notice: Subject to any disclaimer, the term of this patent is extended or adjusted under 35 U.S.C. 154(b) by 299 days.

(21) Appl. No.: 15/527,590

(22) PCT Filed: Nov. 18, 2015

(86) PCT No.: PCT/US2015/061422
§ 371 (c)(1),
(2) Date: May 17, 2017

(87) PCT Pub. No.: WO2016/081653
PCT Pub. Date: May 26, 2016

(65) Prior Publication Data
US 2017/0361007 A1     Dec. 21, 2017

Related U.S. Application Data

(60) Provisional application No. 62/081,896, filed on Nov. 19, 2014.

(51) Int. Cl.
*A61M 1/16*     (2006.01)
*B01D 53/22*    (2006.01)
*B01D 69/02*    (2006.01)
*B01D 69/12*    (2006.01)
*A61M 1/26*     (2006.01)
*B01D 71/70*    (2006.01)

(52) U.S. Cl.
CPC .......... *A61M 1/1698* (2013.01); *A61M 1/267* (2014.02); *B01D 53/228* (2013.01);
(Continued)

(58) Field of Classification Search
CPC ........ A61M 1/1698; A61M 2202/0478; B01D 2325/02; B01D 2325/20; B01D 69/02
See application file for complete search history.

(56) References Cited

U.S. PATENT DOCUMENTS 5,294,401 A    3/1994  Hagiwara
7,695,775 B2   4/2010  Kobrin et al.
(Continued)

FOREIGN PATENT DOCUMENTS

WO    03/102133    12/2003
WO    2005/118018  12/2005
WO    2013/026148   2/2013

OTHER PUBLICATIONS

Bakker et al. (2003) "Improvement of porous silicon based gas sensors by polymer modification," Physica Status Solidi, 197(2): 378-381.
(Continued)

*Primary Examiner* — Leslie R Deak
(74) *Attorney, Agent, or Firm* — Edward J. Baba; Shweta Chandra; Bozicevic, Field & Francis LLP

(57) ABSTRACT

Provided herein is a gas exchange composite membrane and methods of making the same. The gas exchange composite membrane may find use in a method of exchanging gas with blood in a subject in need of blood oxygenation support, which method is also disclosed. Also provided herein are systems and kits that find use in performing the methods of exchanging gas with blood.

21 Claims, 20 Drawing Sheets

(52) U.S. Cl.
CPC .............. *B01D 69/02* (2013.01); *B01D 69/12* (2013.01); *B01D 71/70* (2013.01); *A61M 2202/0478* (2013.01); *A61M 2209/088* (2013.01); *B01D 2257/104* (2013.01); *B01D 2325/02* (2013.01); *B01D 2325/04* (2013.01); *B01D 2325/20* (2013.01)

(56) References Cited

U.S. PATENT DOCUMENTS

| | | |
|---|---|---|
| 2006/0093836 A1 | 5/2006 | Huang et al. |
| 2011/0056882 A1 | 3/2011 | Borenstein et al. |
| 2011/0087187 A1 | 4/2011 | Beck |
| 2013/0197420 A1 | 8/2013 | Fissell, IV et al. |

OTHER PUBLICATIONS

Belhousse et al. (2010) "Electrochemical grafting of poly (3-hexylthiophene) on porous silicon for gas sensing", Surface and Interface analysis John Wiley & Sons Ltd., 42(6-7):1041-1045.

Burgess et al. (2008) "Towards microfabricated biohybrid artificial lung modules for chronic respiratory support", Biomedical Microdevices, Kluwer Academic Publishers, 11(1);117-127.

Chiboub et al. (2010) "Chemical and electrochemical rafting of polyaniline on aniline-terminated porous silicon", Surface and interface analysis John Wiley & Sons Ltd., 42(6-7):1342-1346.

Kung et al. (2008) "Microchannel technologies for artificial lungs: (2) screen-filled wide rectangular channels.", Asaio Journal (American Society for Artificial Internal Organs:1992), 54(4):383-389.

Huh et al. (2013) "Microfabrication of human organs-on-chips," Nature protocols 8(11):2135-2157.

Leslie et al. (2014) "A bioinspired omniphobic surface coating on medical devices prevents thrombosis and biofouling," Nature biotechnology 32(11):1134-1140.

Park et al. (2009) "Micropatterning of poly (dimethylsiloxane) using a photoresist lift-off technique for selective electrical insulation of microelectrode arrays," Journal of Micromechanics and Microengineering 19(6):065016, 18 pgs.

Thangawng et al. (2007) "Bond-Detach Lithography: A Method for Micro/Nanolithography by Precision PDMS Patterning," Small 3(1):132-138.

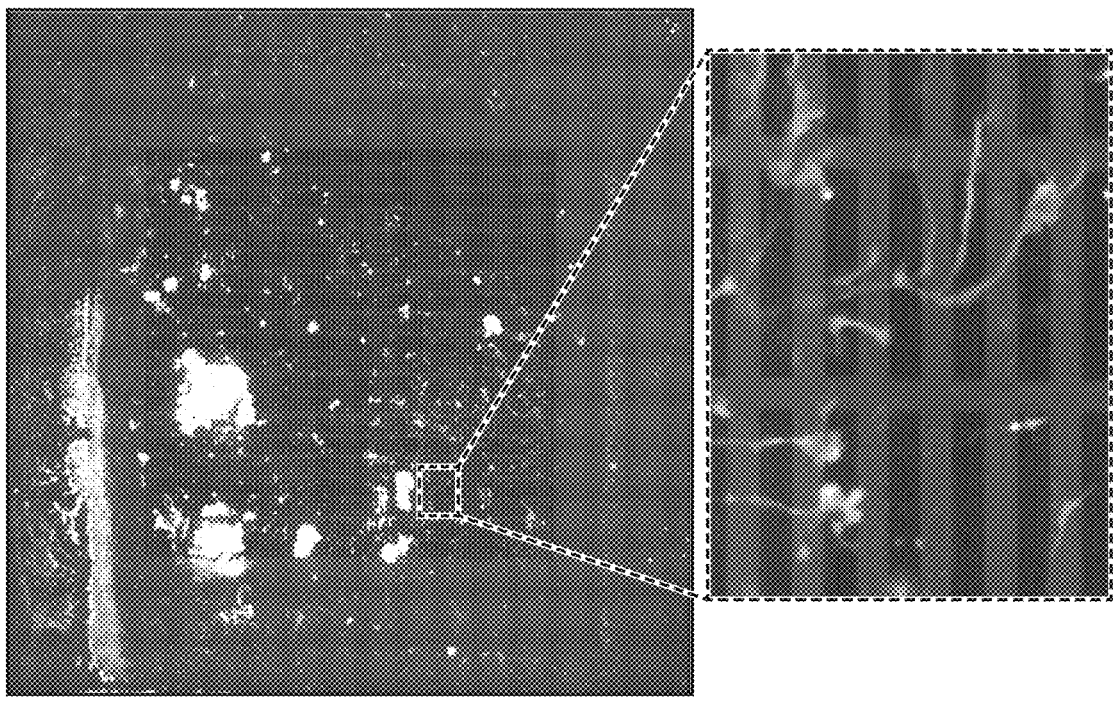
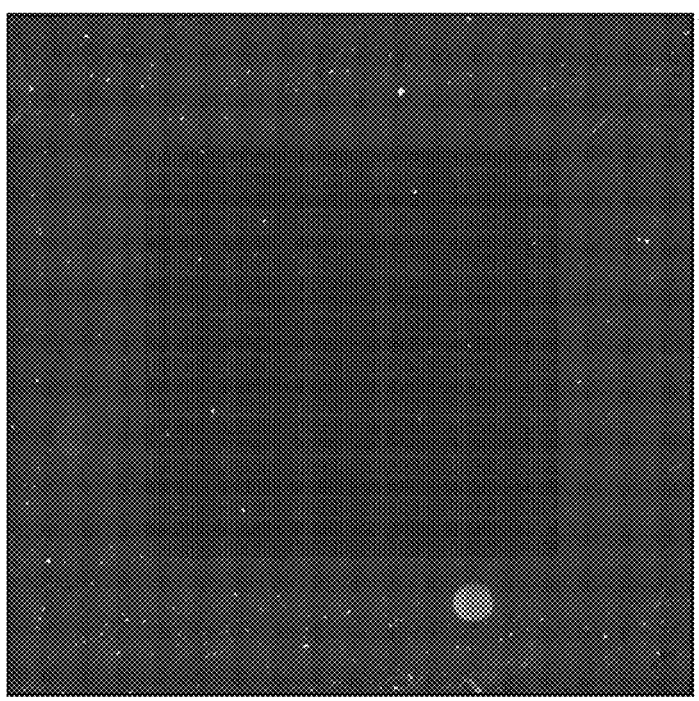

GAS EXCHANGE COMPOSITE MEMBRANES AND METHODS OF USE THEREOF

CROSS-REFERENCE TO RELATED APPLICATIONS

This application claims priority benefit of U.S. Provisional Application No. 62/081,896, filed Nov. 19, 2014, which application is incorporated herein by reference in its entirety and for all purposes.

STATEMENT REGARDING FEDERALLY SPONSORED RESEARCH

This invention was made with government support under Grant Nos. TR000004 and RO1 EB014315, awarded by the National Institutes of Health, and grant no. P50 FD003793, awarded by the Food and Drug Administration. The government has certain rights in the invention.

BACKGROUND

Extracorporeal membrane oxygenation (ECMO) is a respiratory support system wherein blood is pumped out of the body, flowed over a gas permeable membrane to exchange oxygen and carbon dioxide, and returned to the systemic circulation. A typical ECMO system uses a mechanical pump to withdraw deoxygenated blood from the patient, via large diameter (~¼") tubing, through a heat exchanger and oxygenator, before returning oxygen-rich blood to the body.

Unlike mechanical ventilation, which can induce barotrauma by forcing oxygen-rich air into already damaged pulmonary alveoli, ECMO directly oxygenates blood via a synthetic membrane, allowing the lungs to heal. ECMO allows patients to rest and recover from traumatic injury, disease-induced acute respiratory distress, or prepare for lung transplant.

SUMMARY

Provided herein is a gas exchange composite membrane and methods of making the same. The gas exchange composite membrane may find use in a method of exchanging gas with blood in a subject in need of blood oxygenation support, which method is also disclosed. Also provided herein are systems and kits that find use in performing the methods of exchanging gas with blood.

A gas exchange composite membrane of the present disclosure may include: i) a non-porous, gas-permeable, polymeric membrane defining a first surface and a second surface opposite the first surface; and ii) a non-compliant, microporous membrane defining a third surface and a fourth surface opposite the third surface, wherein the microporous membrane includes one or more gas diffusion windows, each containing a network of struts defining walls of a plurality of micropores, each micropore extending from the third surface to the fourth surface; and the third surface is attached to the second surface, wherein the first surface of the polymeric membrane provides an antithrombotic surface for gas exchange over the one or more gas diffusion windows, between blood flowing along the first surface and a gas at the second surface. In some embodiments, the first surface is substantially flat over the one or more gas diffusion windows. In some embodiments, the composite membrane has an oxygen gas permeability against air of 5 mL STP/cmHg/m²/min or more. In some embodiments, the composite membrane has a carbon dioxide gas permeability against air of 20 mL STP/cmHg/m²/min or more. In some embodiments, the composite membrane has an oxygen gas transfer rate against blood of 0.5 mL STP/cmHg/m²/min or more, at an average blood flow speed over the first surface in the range of about 1.0 to about 10 mm/sec. In some embodiments, the composite membrane has a carbon dioxide transfer rate against blood of 2.0 mL STP/cmHg/m²/min or more, at an average blood flow speed over the first surface in the range of about 1.0 to about 10.0 mm/sec. In some embodiments, the polymeric membrane has an average thickness in the range of 0.01 µm to 100 µm, including 0.1 to 15 µm. In some embodiments, the microporous membrane has an average thickness in the range of 0.001 µm to 50 µm, including 0.1 to 50 µm. In some embodiments, each of the one or more gas diffusion windows has a porosity in the range of 1% to 90%, including 20% to 80%. In some embodiments, the one or more gas diffusion windows overlie an area in the range of 1.0 mm² to 1.0 m². In some embodiments, a strut dividing adjacent micropores of the plurality of micropores have an average width in the range of 0.005 µm to 10 µm, including 0.01 to 5.0 µm. In some embodiments, plurality of micropores is an array of micropores having substantially uniform dimensions. In some embodiments, the array is a regular array of micropores. In some embodiments, a micropore of the plurality of micropores has an average width in the range of 0.005 µm to 50 µm, including 0.01 to 10 µm. In some embodiments, the micropore has an average length in the range of 0.01 µm to 100 µm, including 1.0 to 100 µm. In some embodiments, the polymeric membrane is a polydimethylsiloxane (PDMS)-based polymeric membrane. In some embodiments, the first surface is functionalized with an antifouling agent, an anticoagulant and/or an enzyme. In some embodiments, the first surface is functionalized with polyethylene glycol, perfluorocarbon, heparin, polysulfobetaine, or carbonic anhydrase. In some embodiments, the microporous membrane is a microporous polysilicon, silicon, silicon carbide, or silicon nitride membrane. In some embodiments, the fourth surface includes an anchoring strip that circumscribes each gas diffusion window, wherein the anchoring strip protrudes out relative to areas adjacent the anchoring strip on the fourth surface. In some embodiments, the composite membrane further includes a base substrate attached to the anchoring strip.

Also provided herein is a method of making a gas exchange composite membrane, including: a) forming a non-compliant, microporous membrane defining a first surface; b) forming a multilayered membrane-supporting structure containing a plurality of layers superposed among each other, wherein the multilayered membrane-supporting structure defines a second surface containing a superficial layer of the plurality of superposed layers, and wherein the superficial layer includes a non-porous, gas-permeable, polymeric membrane detachably disposed over an underlying layer; c) bonding the first surface to the second surface; and d) detaching the underlying layer from the non-porous, gas-permeable, polymeric membrane, thereby exposing a third surface of the non-porous, gas-permeable, polymeric membrane, wherein the third surface provides an antithrombotic surface for gas exchange across the composite membrane, between blood flowing along the third surface and a gas at a fourth surface of the non-compliant, microporous membrane opposite the first surface. In some embodiments, the non-porous, gas-permeable, polymeric membrane is a PDMS membrane. In some embodiments, the non-compliant, microporous membrane has an average thickness in the range of 0.01 µm to 100 µm, including 0.5 to 10 µm. In some embodiments, the non-porous, gas-permeable, polymeric membrane has an average thickness in the range of 0.001 µm to 50 µm, including 0.5 to 10 µm. In some embodiments, the non-compliant, microporous membrane is a microporous polysilicon, silicon, silicon carbide, or silicon nitride membrane. In some embodiments, the bonding includes plasma bonding, wet chemistry, or physical attachment of the first surface to the second surface.

In any embodiment, the forming the non-compliant, microporous membrane may include:
i) depositing a sacrificial layer over a fifth surface of a base substrate, wherein the sacrificial layer is patterned to create one or more anchor regions, each anchor region defining a window;
ii) depositing a non-compliant membrane on the patterned sacrificial layer; iii) etching, including dry or wet etching, the non-compliant membrane deposited on the patterned sacrificial layer within an area defined by the window, to form a network of struts defining walls of a plurality of micropores in the non-compliant membrane; iv) removing the base substrate over the area defined by the window; and v) removing the sacrificial layer over the area defined by the window. In some embodiments, the base substrate is a silicon or glass base substrate. In some embodiments, the sacrificial layer is a silicon dioxide or silicon nitride layer. In some embodiments, depositing the sacrificial layer includes using thermal oxidation. In some embodiments, the sacrificial layer has a thickness in the range of 0.005 to 10 µm, including 0.1 to 10 µm. In some embodiments, the dry etching the non-compliant membrane includes forming a mask layer comprising a photoresist over the non-compliant membrane, wherein the photoresist is patterned to be present over areas of the non-compliant membrane corresponding to the network of struts. In some embodiments, the dry etching the non-compliant membrane includes reactive ion etching. In some embodiments, the removing the base substrate includes using front-to-back alignment and deep reactive ion etching. In some embodiments, the removing the sacrificial layer includes contacting the sacrificial layer with an acid.

In any embodiment, the forming the multilayered membrane-supporting structure may include i) depositing a transitory polymeric membrane over a sixth surface of a support substrate, wherein the transitory polymeric membrane defines a seventh surface opposite an eighth surface and contacting the sixth surface of the support substrate. In some embodiments, the support substrate is a support silicon substrate. In some embodiments, the sixth surface is a surface treated to passivate the sixth surface against adhesion to the transitory polymeric membrane, and wherein the forming the multilayered membrane-supporting structure further includes; ii) surface-treating the seventh surface to passivate the seventh surface against adhesion to the non-porous, gas-permeable, polymeric membrane; and iii) depositing the non-porous, gas-permeable, polymeric membrane over the surface-treated seventh surface; and iv) detaching the support substrate from the eighth surface. In some embodiments, the transitory polymeric membrane is a transitory PDMS membrane. In some embodiments, the sixth surface is silanized. In some embodiments, the surface treating the seventh surface includes silanizing the seventh surface. In some embodiments, the detaching the underlying layer from the polymeric membrane includes mechanically detaching the transitory polymeric membrane from the non-porous, gas-permeable, polymeric membrane. In some embodiments, the surface treating the seventh surface includes depositing a water-soluble polymer layer over the seventh surface. In some embodiments, the detaching the underlying layer from the polymeric membrane includes contacting the water-soluble polymer layer with water to dissolve the water-soluble polymer layer. In some embodiments, the transitory polymeric membrane is a dissolvable polymeric membrane, and wherein the detaching the underlying layer from the non-porous, gas-permeable, polymeric membrane includes contacting the dissolvable polymeric membrane with a solvent, thereby dissolving the dissolvable polymeric membrane. In some embodiments, the dissolvable polymeric membrane is an epoxy-based dissolvable polymeric membrane. In some embodiments, the dissolvable polymeric membrane is a photoresist membrane. In some embodiments, the dissolvable polymeric membrane is an SU-8 membrane. In some embodiments, the solvent is an organic solvent. In some embodiments, the solvent is acetone.

In any embodiment the third surface may be a functionalized surface.

In any embodiment the method may further include functionalizing a surface of the non-porous, gas-permeable, polymeric membrane.

Also provided herein is a blood oxygenation device that includes: 1) a blood channel comprising a first inlet at a first end and a first outlet at a second end opposite the first end, wherein the blood channel is configured to pass a flow of blood from the first inlet to the first outlet; 2) a first gas channel configured to pass a flow of gas; and 3) a first gas exchange composite membrane of the present disclosure, wherein the first composite membrane is disposed between the blood channel and the first gas channel in a manner sufficient to provide a gas permeable barrier between the blood channel and the first gas channel. In some embodiments, the device further includes: 4) a second gas channel comprising a second inlet at a fifth end and a second outlet at a sixth end opposite the fifth end, wherein the second gas channel is configured to pass a flow of the gas from the second inlet to the second outlet; and 5) a second gas exchange composite membrane, wherein the second composite membrane is disposed between the blood channel and the second gas channel in a manner sufficient to provide a gas permeable barrier between the blood channel and the second gas channel. In some embodiments, the blood channel has a length defined by the distance between the first end and a second end in the range of 0.1 to 300 mm, including 1.0 to 300 mm. In some embodiments, a cross-section in a plane perpendicular to the average direction of flow of the blood in the blood channel is a rectangular cross-section defining a width and a height of the blood channel, wherein an edge of the rectangular cross-section defining the width includes the first surface of the non-porous, gas-permeable, polymeric membrane of the first composite membrane. In some embodiments, the width of the blood channel is in the range of 0.05 to 300 mm, including 0.5 to 300 mm. In some embodiments, the height of the blood channel is in the range of 0.001 to 300 mm, including 0.01 to 2.0 mm. In some embodiments, the ratio of the width to height of the blood channel is in the range of 10 to 1,000. In some embodiments, the gas diffusion windows of the first composite membrane collectively overlie an area in the range of 1.0 $mm^2$ to 0.5 $m^2$. In some embodiments, the blood channel has a volume in the range of 1.0 $mm^3$ to 1.5 $m^3$. In some embodiments, the flow of blood has an average direction that is substantially perpendicular to a direction of the flow of gas. In some embodiments, the flow of blood has an average direction that is substantially parallel to a direction of the flow of gas. In some embodiments, the device is stackable. In some embodiments, the blood channel includes a tapered inlet. In some embodiments, the blood channel includes a tapered outlet. In some embodiments, the blood channel includes a polymeric or metal channel. In some embodiments, the blood channel includes a polycarbonate, polyurethane or silicone channel. In some embodiments, the blood channel is a PDMS channel. In some embodiments, the blood channel is a titanium alloy channel. In some embodiments, the channel includes a surface that is functionalized. In some embodiments, the surface is functionalized with polyethylene glycol, perfluorocarbon and/or heparin.

Also provided herein is a method of exchanging gas with blood including a first dissolved gaseous compound, the method including: (A) pumping blood from a circulatory system of a subject to an extracorporeal blood circuit to generate a circulating flow of the blood, the extracorporeal blood circuit comprising one or more non-circuitous blood channels of one or more blood oxygenating devices, each blood channel defining a first end and a second end opposite the first end, wherein each of the blood oxygenating devices includes: a gas channel configured to pass a flow of gas, wherein the gas includes a second gaseous compound; one or more gas exchange composite membranes configured to exchange gaseous compounds between the blood and the gas across a planar surface separating the blood channel and the gas channel; and (B) flowing the gas through the gas channel, thereby exchanging gaseous compounds between the circulating flow of the blood and the gas. In some embodiments, a cross-section in a plane perpendicular to the average direction of the circulating flow of the blood in the blood channel is a rectangular cross-section defining a width and a height of the blood channel, wherein an edge of the rectangular cross-section defining the width includes the planar surface separating the blood channel and the gas channel. In some embodiments, the width of the blood channel is in the range of 0.001 to 300 mm, including 0.5 to 300 mm. In some embodiments, the height of the blood channel is in the range of 0.001 to 300 mm, including 0.01 to 2.0 mm. In some embodiments, the ratio of the width to height of the blood channel is in the range of 10 to 1,000. In some embodiments, the partial pressure of the second gaseous compound in the gas is 20 cmHg or more. In some embodiments, blood is pumped at a flow rate in the range of 0.1 to 100 ml/min. In some embodiments, the flow of blood within the blood channel has a maximum shear stress of 1,000 dyne cm$^{-2}$ or less. In some embodiments, the flow of blood across each of the non-circuitous blood channels has a hydraulic pressure drop between the first end and the second end of 100 mmHg or less. In some embodiments, the one or more blood oxygenating devices has an oxygen transfer rate between the gas and the blood of 0.5 mL STP/cmHg/m$^2$/min or more, at an average blood flow rate in the rage of about 0.1 to 1.0 mL/min. In some embodiments, the one or more blood oxygenating devices has an carbon dioxide transfer rate between the gas and the blood of 2.0 mL STP/cmHg/m$^2$/min or more, at an average blood flow speed over the first surface in the range of about 0.1 to 1.0 mL/min. In some embodiments, the one or more blood oxygenating devices collectively have a gas exchange surface area in the range of 0.01 to 10 m$^2$, including 0.1 to 5 m$^2$. In some embodiments, the one or more blood oxygenating devices includes one or more gas exchange composite membranes.

Provided herein is a system for exchanging gas with blood using one or more blood oxygenation devices of the present disclosure. In some embodiments, the one or more blood oxygenating devices collectively provide a gas exchange surface area in the range of 0.1 to 5 m$^2$. In some cases, the one or more blood oxygenation devices are configured to be wearable.

Also provided is a kit that includes a gas exchange composite membrane of the present disclosure.

BRIEF DESCRIPTION OF THE FIGURES

The skilled artisan will understand that the drawings, described below, are for illustration purposes only. The drawings are not intended to limit the scope of the present teachings in any way.

FIGS. 15A and 15B are a collection of images showing a surface profile of a gas exchange composite membrane after flowing blood through a blood oxygenation device that includes the gas exchange composite membrane.

DEFINITIONS

Figure 1:
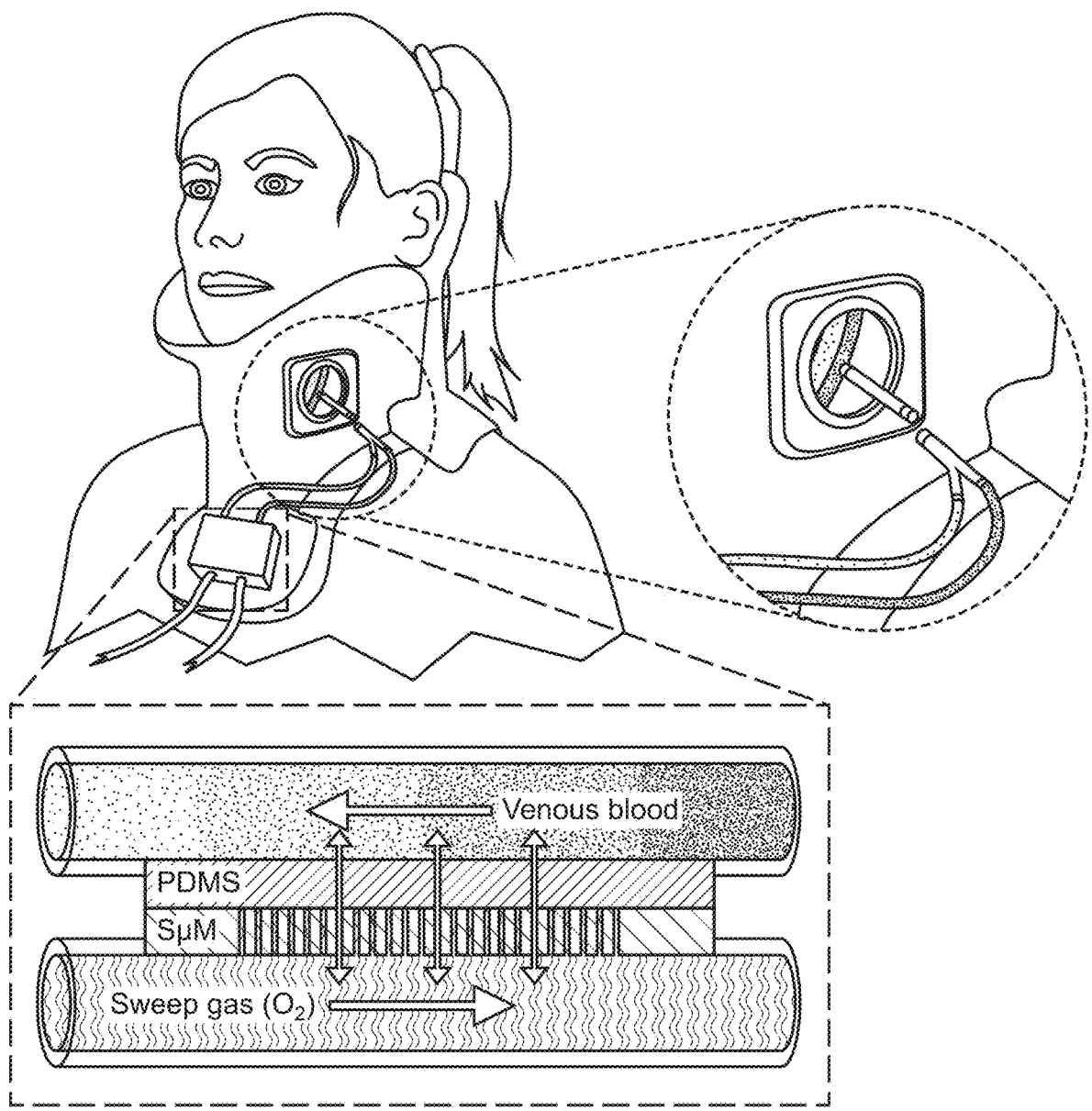
FIG. 1 is a schematic drawing showing a blood oxygenation device that includes a gas exchange composite membrane, according to embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

"Substantially" as used herein, may be applied to modify any quantitative representation that could permissibly vary without resulting in a change in the basic function to which it is related. For example, a direction of flow of gas may be somewhat off-perpendicular from the direction of flow of blood if the gas exchange properties between the gas and the blood are not materially altered.

"Blood oxygenation" as used herein, may refer to a general process of exchanging gas with blood of a subject to achieve gas exchange that typically occurs in the lung. Blood oxygenation may include increasing the oxygen content of blood and/or reduce the carbon dioxide content of blood.

"Non-porous" as used herein, may be applied to describe a property of a structure or material that is not permeable to liquids under normal conditions for use intended in the present disclosure.

"Polymeric" as used herein, may be used to describe an organic compound composed of repeating units of one or more monomers containing carbon and hydrogen atoms The monomers can also include other atoms such as Si, O, N, P, and S. A polymer may have a solid bulk polymer matrix.

"Membrane" and "film" are used interchangeably to refer to a solid material that, when laid out on a planar surface, can have a substantially planar geometry. The membrane may have one dimension (the "depth" or "thickness") that is considerably shorter than the other two dimensions (the "width" and "length"), so as to form the planar geometry. The "surface" of a membrane refers to the area of the membrane defined by edges along the width and the length.

"Non-compliant" as used herein, may be applied to describe the property of a structure or material that does not substantially deform under force experienced by the structure or material under normal conditions for use intended in the present disclosure. A non-compliant material may have a Young's modulus (E) of 100 GPa or more, e.g., 120 GPa or more, 140 GPa or more, including 160 GPa or more.

"Microporous" may be used to describe a pore whose opening size has a lateral dimension (i.e., the diameter, width, or length) that is at a micrometer scale (i.e., between 1.0 to 1,000 µm).

A "network" as used in reference to struts defining micropores, may describe struts that are interconnected.

An "array", as used herein, refers to an arrangement of elements where the location of each element is spatially defined (i.e, not random). A "regular array" refers to an array that contains a uniformly repeated arrangement of elements.

"Superficial" as used herein, may be applied to describe a layer within a multi-layered structure that is either the first or the last layer. Thus, a superficial layer of a multi-layered structure is contacted with an underlying layer on only one surface.

"Superposed" as used herein, may be used to describe a relative position between at least two structures where a first surface of a first structure contacts a second surface of a second structure, and substantially covers the second surface.

"Extracorporeal", as used herein, may be applied to describe a physiological process of a body that is replaced or supplemented by an artificial system that can perform at least some aspects of the physiological process. For a continuous physiological process, such as circulation of blood, the artificial system can be configured to continuously perform the physiological process by having physical access to the body part relevant for the physiological process.

"Circulating", as used herein, may be used to describe a unidirectional movement of a material through a closed system, where material starting at a location in the closed system returns to the same location after moving through the closed system.

"Non-circuitous" as used herein, may be applied to describe a shape or path through a structure that does not meander or turn significantly. Thus, in some cases, "non-circuitous" may be interchangeable with "substantially straight."

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

DETAILED DESCRIPTION

As summarized above, the present disclosure provides a gas exchange composite membrane that may be used to oxygenate blood. The present gas exchange composite membrane may find use in providing a compact, wearable or portable system for extracorporeal membrane oxygenation, for patients in need of blood oxygenation and carbon dioxide removal during acute respiratory distress (FIG. 1).

The gas exchange composite membrane may include a non-porous, gas-permeable, polymeric membrane attached to a surface of a non-compliant, microporous membrane. The microporous membrane may include micron-sized pores that extend through the microporous membrane and are defined by struts that form the walls of the micropores. Thus, the attachment between the polymeric membrane and the microporous membrane includes attachment between the polymeric membrane and the struts of the microporous membrane.

Figure 5:
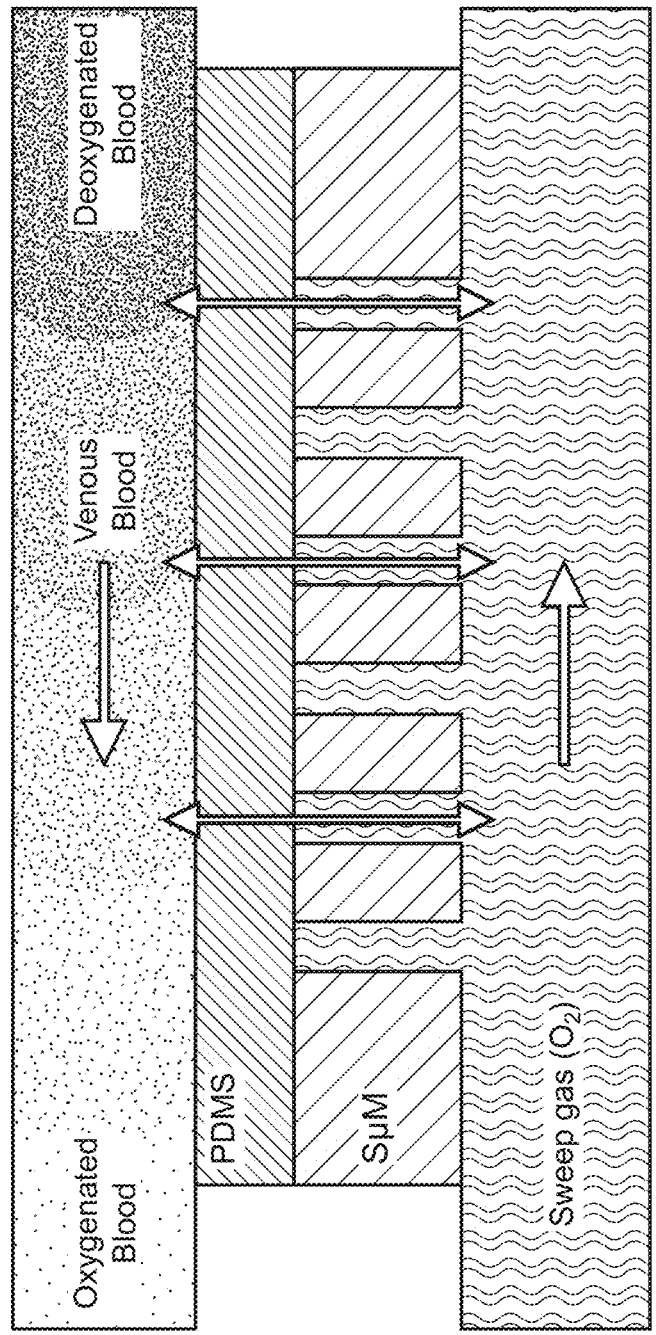
FIG. 5 is a schematic diagram showing a configuration of blood and gas flowing over a gas exchange composite membrane, according to embodiments of the present disclosure.

Blood may flow over the surface of the composite membrane on the non-porous, gas-permeable, polymeric membrane side, and gaseous compounds may be exchanged between the blood flow and a gas on the other side of the composite membrane that has the non-compliant, microporous membrane (FIG. 5). Because the non-porous, gas-permeable, polymeric membrane is attached to the non-compliant, microporous membrane, the latter serves as a structural support to significantly reduce gas pressure-induced deformation of the polymeric membrane that would create obstructions to the blood flow over the polymeric membrane, and prevent collapse of the blood flow compartment due to the gas pressure. The micropores define areas through which gas can diffuse, across the composite membrane, and thus provide a sufficient diffusion surface area to oxygenate blood. At the same time, the polymeric membrane prevents or reduces the risk of gas embolism in the flowing blood even at high pressure gradients of gas across the composite membrane. The polymeric membrane also prevents blood components (e.g., cells, proteins, plasma, etc) from entering the gas flow compartment.

Further aspects of the present composite membrane are now described.

Composite Membranes

Figure 3A:
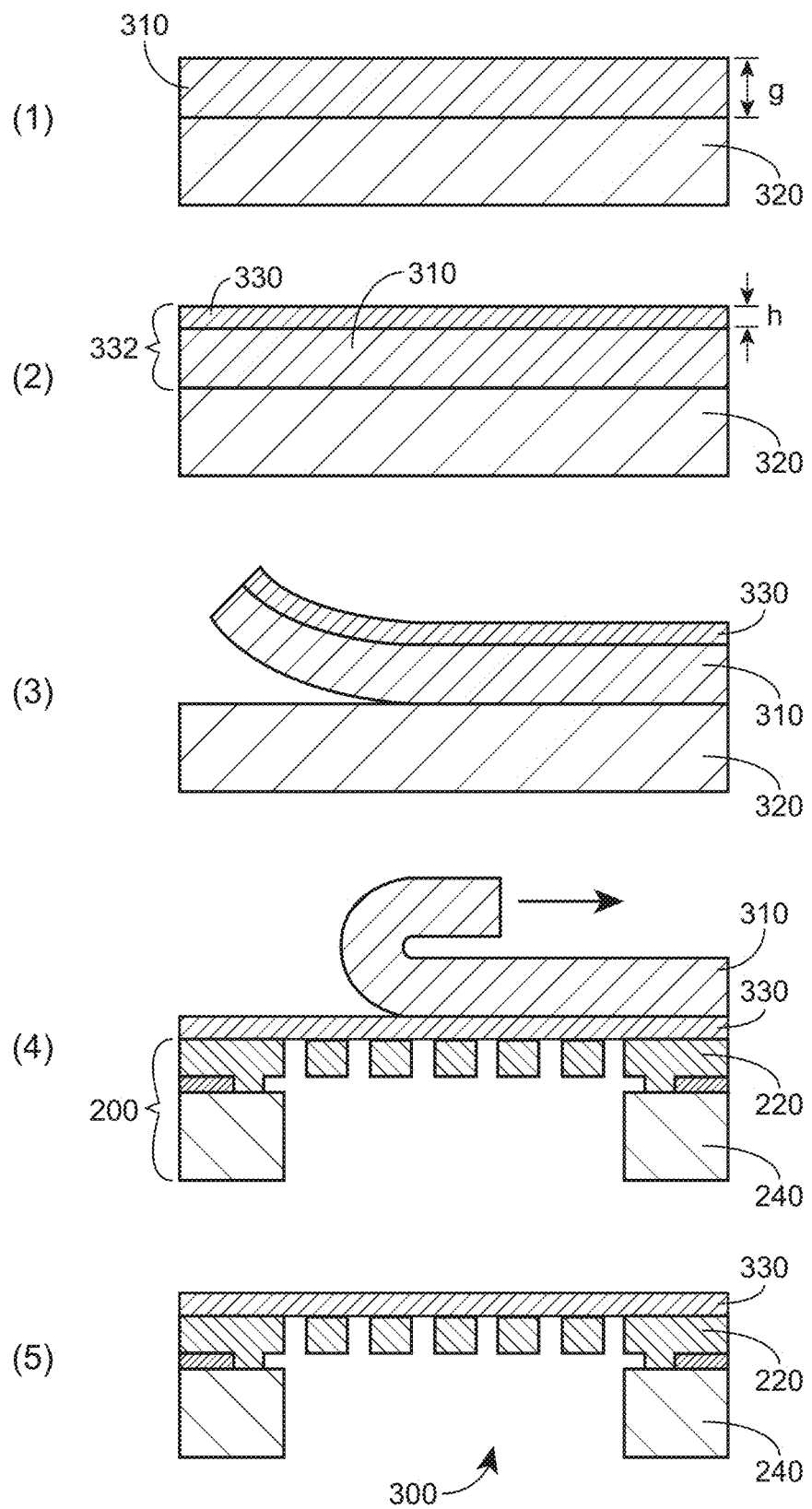
FIGS. 3A-3C are schematic diagrams showing processes of making a gas exchange composite membrane, according to embodiments of the present disclosure.

The gas exchange composite membrane of the present disclosure may be described with reference to the accompanying figures. With reference to FIG. 3A, a schematic diagram of a gas exchange composite membrane 300 is shown. The gas exchange composite membrane may include a non-porous, gas-permeable, polymeric membrane 330 attached to a surface of a non-compliant, microporous membrane 220. The polymeric membrane 330 may be non-porous, such that the liquids, such as blood cannot pass through the polymeric membrane. The polymeric membrane may include a suitable material and have a suitable thickness ("h") to allow sufficient gas permeability, e.g., oxygen and/or carbon dioxide permeability, across the composite membrane, between blood on the polymeric membrane side and gas on the microporous membrane 220 side. The polymeric membrane can be made of any suitable material to allow gas diffusion, and to have a controllable thickness during manufacture.

The top surface of the non-porous, gas-permeable, polymeric membrane 330 may be a substantially flat surface. The substantially flat surface of the polymeric membrane can provide a controlled surface over which blood flows, and allow control of blood shear, which is a factor in thrombus formation and hemolysis. Thus, the planar surface of the gas exchange composite membrane 300 over which blood flows, i.e., the surface of the non-porous, gas-permeable, polymeric membrane opposite the surface attached to the non-compliant, microporous membrane 220, can provide a surface with reduced risk of thrombus formation and/or hemolysis than a polymeric membrane surface that is not supported by a microporous membrane.

The microporous membrane 220 has dimensions, e.g., thickness, and is made of material sufficient to render the microporous membrane non-compliant in response to force that the microporous membrane may experience during normal use of the composite membrane for gas exchange with blood. The non-compliant microporous membrane can have a stiffness that resists deformation when pressure is applied to the polymeric membrane 330 attached to the non-compliant microporous membrane. Thus, in some cases, the microporous membrane is a substantially rigid membrane. The thickness ("b") of the microporous membrane is a suitable thickness to provide sufficient stiffness to the microporous membrane. The microporous membrane can be made of any suitable material to provide the structural support to the polymeric membrane and to have controllable thickness and pore sizes during manufacture.

Figure 2:
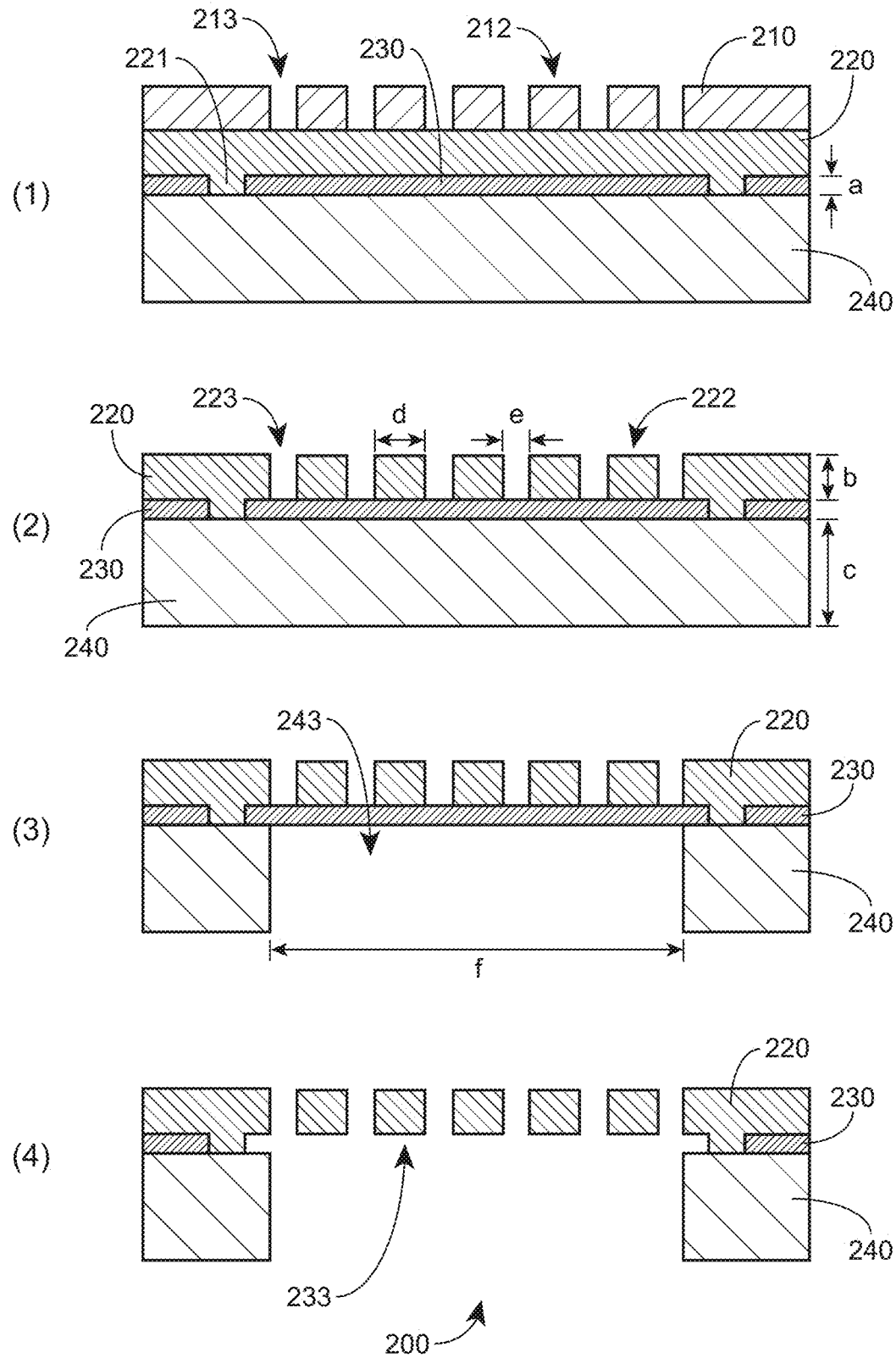
FIG. 2 is a schematic diagram showing a process of making a non-compliant, microporous membrane for use in a gas exchange composite membrane, according to embodiments of the present disclosure.

With reference to FIG. 2, (4), the non-compliant, microporous membrane 220 may include a number of struts 222 that define walls of a number of micropores 223. The struts may be interconnected to form a network of struts (see also, FIG. 4B). As such, the shape of the struts and their interconnectivity can define the shape and the pattern of the micropores. The micropores each extend from one surface of the microporous membrane to the other surface. The path through the center of a pore may follow any suitable path, and may be substantially perpendicular to the plane of the surfaces (see also, FIG. 4C). Gas exchange can occur across the area of the composite membrane 300 that corresponds to the area where the struts define the micropores in the non-compliant, microporous membrane 220, which area can be defined as a gas diffusion window. The non-compliant, microporous membrane may be attached to a base substrate 240 in a manner such that the base substrate does not occlude the gas diffusion window.

The polymeric membrane 330 can have any suitable thickness (FIG. 3A, "h"). In some cases, the average thickness of the polymeric membrane is 0.1 μm or more, e.g., 0.5 μm or more, 1.0 μm or more, 2.0 μm or more, 3.0 μm or more, including 4.0 μm or more, and is 15 μm or less, e.g., 10 μm or less, 8.0 μm or less, 6.0 μm or less, including 5.0 μm or less. In certain embodiments, the average thickness of the polymeric membrane is in the range of 0.1 to 25 μm, e.g., 0.5 to 15 μm, 1.0 to 10 μm, 2.0 to 8.0 μm, including 3.0 to 6.0 μm.

The microporous membrane 220 can have any suitable thickness (FIG. 2, "b"). In some cases, the average thickness of the microporous membrane is 0.1 μm or more, e.g., 0.2 μm or more, 0.5 μm or more, 1.0 μm or more, including 5.0 μm or more, and is 50 μm or less, e.g., 20 μm or less, 10 μm or less, 5.0 μm or less, including 4.0 μm or less. In certain embodiments, the average thickness of the microporous membrane is in the range of 0.1 to 100 μm, e.g., 0.2 to 50 μm, 0.2 to 20 μm, 0.2 to 10 μm, including 0.5 to 5.0 μm.

The gas diffusion window of the microporous membrane 220 can have any suitable porosity. In some cases, the gas diffusion window has a porosity of 20% or more, e.g., 30% or more, 40% or more, 50% or more, including 60% or more, and is 80% or less, e.g., 70% or less, 60% or less, including 50% or less. In some cases, the gas diffusion window has a porosity in the range of 20 to 80%, e.g., 30 to 70%, including 30 to 60%.

The gas diffusion window of the microporous membrane 220 can overlie any suitably-sized area of the present composite membrane 300. In some cases, the gas diffusion window overlies an area of 1.0 mm$^2$ or more, e.g., 10 mm$^2$ or more, 100 mm$^2$ or more, 1,000 mm$^2$ or more, including 0.01 m$^2$ or more, and overlies an area of 1.0 m$^2$ or less, e.g., 0.1 m$^2$ or less, 0.01 m$^2$ or less, including 1,000 mm$^2$. In some cases, the gas diffusion window overlies an area in the range of 1.0 mm$^2$ to 1.0 m$^2$, e.g., 10 mm$^2$ to 0.1 m$^2$, 100 mm$^2$ to 0.1 m$^2$, including 1,000 mm$^2$ to 0.1 m$^2$.

The width (FIG. 2, "d") of a strut dividing adjacent micropores can have any width. In certain cases, the average width of a strut dividing adjacent micropores is 0.01 μm or more, e.g., 0.1 μm or more, 0.2 μm or more, 0.3 μm or more, including 0.4 μm or more, and is 5.0 μm or less, 4.0 μm or less, 3.0 μm or less, 2.0 μm or less, including 1.0 μm or less. In certain cases, the average width of a strut dividing adjacent micropores is in the range of 0.01 to 5.0 μm, e.g., 0.1 to 4.0 μm, 0.2 to 3.0 μm, including 0.2 to 2.0 μm.

The micropores 223 may be arranged across the surface of the microporous membrane in any suitable manner. In some cases, the micropores are an array of micropores. In some cases, the micropores have a uniform width and lengths across the microporous membrane. In certain cases, the micropores are in a regular array.

The pore shape of the micropores 223 may have any suitable shape and dimensions. The pores shape of the micropores may be substantially circular, oval, rectangular, square, triangular, etc. A micropore may have an average width (FIG. 2, "e") of 0.01 μm or more, e.g., 0.1 μm or more, 0.2 μm or more, 0.3 μm or more, 0.4 μm or more, including 0.5 μm, 10.0 μm or more, and may have an average width of 10 μm or less, e.g., 5.0 μm or less, 3.0 μm or less, 2.0 μm or less, 1.0 μm or less, including 0.8 μm or less. In certain embodiments, a micropore may have an average width in the range of 0.01 to 10 μm, e.g., 0.1 to 10 μm, 0.2 to 5.0 μm, 0.2 to 3.0 μm, 0.3 to 1.0 μm, including 0.3 to 0.8 μm. A micropore may have an average length of 1.0 μm or more, e.g., 2.0 μm or more, 3.0 μm or more, 4.0 μm or more, including 5.0 μm or more, and may have an average width of 100 μm or less, e.g., 50 μm or less, 30 μm or less, 20 μm or less, 10 μm or less, including 8.0 μm or less. In certain embodiments, a micropore may have an average width in the range of 1.0 to 100 μm, e.g., 2.0 to 50 μm, 2.0 to 30 μm, 3.0 to 20 μm, 3.0 to 10 μm, including 3.0 to 8.0 μm.

The polymeric membrane 330 may be any suitable polymeric material for use in the present composite membrane as a non-porous, gas-permeable polymeric membrane. The polymeric membrane can be a biocompatible polymeric membrane. Suitable material for a non-porous, gas-permeable polymeric membrane include, but are not limited to polypropylene, polymethylpentene, polyisoprene, polybutadiene, polychloroprene, polyisobutylene, poly(styrene-butadiene-styrene), polyurethane, silicon, poly(bis(fluoroalkoxy)phosphazene), poly(carboranesiloxanes), poly(acrylonitrile-butadiene), poly(1-butene), poly(chlorotrifluoroethylene-vinylidene fluoride) copolymers, poly(ethyl vinyl ether), poly(vinylidene fluoride), poly(vinylidene fluoride-hexafluoropropylene) copolymer, polyvinylchloride (PVC), polysulfone, polycarbonate, polymethylmethacrylate (PMMA), or polytetrafluoroethylene.

In some cases, the polymeric membrane 330 is a silicone membrane. In some cases, the polymeric membrane is a vulcanizing silicone, e.g., a room temperature vulcanizing (RTV) silicone. In some cases, the polymeric membrane is polydimethylsiloxane (PDMS), and derivatives thereof. In some cases, the polymeric membrane may include any solid PDMS polymer composed of at least one dimethylsiloxane monomer. In some instances, at least two dimethylsiloxane monomers are used to make the PDMS substrate. The monomer mixtures may contain additional components, such as other monomers or a catalyst, such as platinum. Various monomer mixtures are commercially available and include, for example, Sylgard® 184 (Dow Corning Corporation, Midland, Mich., United States), RTV 615 (Sil-Mid limited, Coleshill, West Midlands, United Kingdom) and ELASTOSiL® RT 601 (Wacker Chemie AG, San Jose, Calif., United States). The ratio of monomer to crosslinker used to make the polymer membrane containing PDMS may be any suitable ratio. In some cases, the ratio of monomer to crosslinker is 1 or more, e.g., 2 or more, 3 or more, 4 or more, 5 or more, including 8 or more, and is 20 or less, e.g., 15 or less, 13 or less, 12 or less, 11 or less, including 10 or less. In some cases, the ratio of monomer to crosslinker is in the range of 1 to 20, e.g. 1 to 15, 2 to 13, including 2 to 12. The PDMS may be cured at any suitable temperature. In some cases, the PDMS is cured at 60° C. or more, e.g., 70° C. or more, 75° C. or more, including 80° C. or more, and is cured at 90° C. or less, e.g., 85° C. or less, including 80° C. or less. In some cases, the PDMS is cured at a temperature in the range of 60 to 90° C., e.g., 70 to 90° C., including 75 to 85° C. The PDMS may be cured for any suitable amount of time. In some cases, the PDMS is cured for 30 min or more, e.g., 1.0 hr or more, 1.5 hrs or more, including 2.0 hrs or more, and is cured for 24 hrs or less, e.g., 12 hrs or less, 8.0 hrs or less, 4.0 hrs or less, including 2.0 hrs or less. In some cases, the PDMS is cured for 0.5 to 24 hrs, e.g., 1.0 to 12 hrs, 1.0 to 8.0 hrs, including 1.0 to 4.0 hrs.

The surface of the polymeric membrane 330, e.g., the surface opposite the surface attached to the microporous membrane 220, may be a surface functionalized to reduce fouling of the membrane surface, reduce coagulation of blood on the surface of the membrane surface, and/or increase the efficiency of gas exchange of a gaseous compound in the blood, such as carbon dioxide. In some cases, the surface of the polymeric membrane is functionalized with polyethylene glycol, perfluorocarbon, heparin, and/or carbonic anhydrase. Any other suitable functionality may be provided to the surface of the polymeric membrane.

The microporous membrane 220 may include any suitable material for use as a non-compliant microporous membrane. Suitable materials include, but are not limited to, ceramics, glass, glass polymers, glass/polymer materials, metals (e.g., chromium, cobalt, gold, molybdenum, nickel, stainless steel, titanium, tungsten steel, and the like), molded plastics, polysilicon, silicon-based organic polymers.

In some cases, the composite membrane 300 includes an anchoring strip 221 that protrudes from the surface of the microporous membrane 220 opposite the surface attached to the polymeric membrane 330. The anchoring strip may protrude out relative to areas adjacent the anchoring strip on the surface of the microporous membrane by any suitable distance, and may protrude out by 0.1 µm or more, e.g., 0.2 µm or more, 0.5 µm or more, 0.75 µm or more, including 1.0 µm or more, and may protrude out by 5.0 µm or less, e.g., 4.0 µm or less, 3.0 µm or less, including 2.0 µm or less. In some cases, the anchoring strip may protrude out by a range of 0.1 to 5.0 µm, e.g., 0.2 to 4.0 µm 0.5 to 3.0 µm, including 0.75 to 2.0 µm. The anchoring strip may circumscribe a gas diffusion window of the composite membrane. In some cases, the composite membrane includes a base substrate 240 attached to the anchoring strip. The base substrate is any suitable base substrate on which to construct the microporous membrane. In some cases, the base substrate is a silicon wafer.

The base substrate 240 may have any suitable thickness ("c" in FIG. 2). In some embodiments, the base substrate has a thickness of 10 µm or more, e.g., 50 µm or more, 100 µm or more, 200 µm or more, 300 µm or more, including 400 µm or more, and has a thickness of 1,000 µm or less, e.g., 800 µm or less, 600 µm or less, including 500 µm or less. In some cases, the base substrate has a thickness in the range of 10 to 1,000 µm, e.g., 50 to 800 µm, 100 to 600 µm, including 200 to 600 µm.

The composite membrane can have any suitable permeability to gaseous compounds that are to be exchanged with, e.g., blood. Gas permeability may be measured using a dry flow cell connected to a pressurized gas supply containing the gaseous compound of interest, and a bubble flow meter. In some embodiments, the present composite membrane has an oxygen gas permeability against air of 5 mL Standard temperature and pressure (STP)/cmHg/m$^2$/min or more, e.g., 7 mL STP/cmHg/m$^2$/min or more, 9 mL STP/cmHg/m$^2$/min or more, 10 mL STP/cmHg/m$^2$/min or more, including 11 mL STP/cmHg/m$^2$/min or more, and has an oxygen gas permeability against air of 50 mL STP/cmHg/m$^2$/min or less, e.g., 40 mL STP/cmHg/m$^2$/min or less, 30 mL STP/cmHg/m$^2$/min or less including 20 mL STP/cmHg/m$^2$/min or less. In some embodiments, the present composite membrane has an oxygen gas permeability against air in the range of 5 to 50 STP/cmHg/m$^2$/min, e.g., 5 to 40 mL STP/cmHg/m$^2$/min, 5 to 30 mL STP/cmHg/m$^2$/min, including 10 to 20 mL STP/cmHg/m$^2$/min.

In some embodiments, the present composite membrane has a carbon dioxide gas permeability against air of 20 mL STP/cmHg/m$^2$/min or more, e.g., 40 mL STP/cmHg/m$^2$/min or more, 50 mL STP/cmHg/m$^2$/min or more, 55 mL STP/cmHg/m$^2$/min or more, including 60 mL STP/cmHg/m$^2$/min or more, and has a carbon dioxide gas permeability against air of 200 mL STP/cmHg/m$^2$/min or less, e.g., 150 mL STP/cmHg/m$^2$/min or less, 100 mL STP/cmHg/m$^2$/min or less including 90 mL STP/cmHg/m$^2$/min or less. In some embodiments, the present composite membrane has a carbon dioxide gas permeability against air in the range of 20 to 200 STP/cmHg/m$^2$/min, e.g., 40 to 150 mL STP/cmHg/m$^2$/min, 50 to 100 mL STP/cmHg/m$^2$/min, including 60 to 90 mL STP/cmHg/m$^2$/min.

The present composite membrane has any suitable oxygen gas transfer rate against blood at an average blood flow speed over the first surface in the range of about 1.0 to about 10 mm/sec. In some embodiments, the composite membrane has an oxygen gas transfer rate against blood of 0.5 mL STP/cmHg/m$^2$/min or more, e.g., 1.0 mL STP/cmHg/m$^2$/min or more, 1.5 mL STP/cmHg/m$^2$/min or more, including 2.0 mL STP/cmHg/m$^2$/min or more, and has an oxygen gas transfer rate against blood of 10 mL STP/cmHg/m$^2$/min or less, e.g., 8.0 mL STP/cmHg/m$^2$/min or less, 6.0 mL STP/cmHg/m$^2$/min or less, 4.0 mL STP/cmHg/m$^2$/min or less, including 3.0 mL STP/cmHg/m$^2$/min or less. In some embodiments, the composite membrane has an oxygen gas transfer rate against blood in the range of 0.5 to 10 mL STP/cmHg/m$^2$/min, e.g., 1.0 to 8.0 mL STP/cmHg/m$^2$/min, 1.5 to 6.0 mL STP/cmHg/m$^2$/min, including 1.5 to 4.0 mL STP/cmHg/m$^2$/min.

In some embodiments, the composite membrane has a carbon dioxide gas transfer rate against blood of 2.0 mL STP/cmHg/m$^2$/min or more, e.g., 2.5 mL STP/cmHg/m$^2$/min or more, 3.0 mL STP/cmHg/m$^2$/min or more, 4.0 mL STP/cmHg/m$^2$/min or more, including 5.0 mL STP/cmHg/m$^2$/min or more, and has a carbon dioxide gas transfer rate against blood of 50 mL STP/cmHg/m$^2$/min or less, e.g., 40 mL STP/cmHg/m$^2$/min or less, 30 mL STP/cmHg/m$^2$/min or less, 20 mL STP/cmHg/m$^2$/min or less, including 10 mL STP/cmHg/m$^2$/min or less. In some embodiments, the composite membrane has a carbon dioxide transfer rate against blood in the range of 2.0 to 50 mL STP/cmHg/m$^2$/min, e.g., 3.0 to 30 mL STP/cmHg/m$^2$/min, 4.0 to 20 mL STP/cmHg/m$^2$/min, including 5.0 to 10 mL STP/cmHg/m$^2$/min.

Methods of making a Composite Membrane

In general terms, the fabrication of a gas exchange composite membrane of the present disclosure includes a) forming a non-compliant, microporous membrane defining a first surface; b) forming a multilayered membrane-supporting structure having a plurality of superposed layers, wherein the multilayered membrane supporting structure defines a second surface of a superficial layer of the plurality of superposed layers, wherein the superficial layer includes a non-porous, gas-permeable, polymeric membrane detachably disposed over an underlying layer; c) bonding the first surface to the second surface; and d) detaching the polymeric membrane from the underlying layer. Various embodiments of making a gas exchange composite membrane of the present disclosure are described with reference to the accompanying drawings.

With reference to FIG. 2, a method of fabricating a non-compliant, microporous membrane 220 of the present composite membrane is described. The method may include constructing a multilayered structure on the front side of a base substrate 240, e.g., a silicon wafer, where a sacrificial layer 230, e.g., a silicon dioxide layer, is deposited over the front side of the base substrate, and a non-compliant membrane 220, e.g., a polysilicon film, is deposited over the sacrificial layer (FIG. 2, step (1)). The sacrificial layer may be patterned to provide anchor regions 221 for the non-compliant membrane to maintain attachment to the base substrate. As would be apparent, the anchor regions may be provided to enclose an area on the base substrate, e.g., circumscribing a rectangular area with a width and a length, thereby dividing the base substrate into a subregion, or a window. Any suitable dimensions and number of windows may be provided on the base substrate.

A photoresist layer 210 may be disposed over the non-compliant membrane 220 (FIG. 2, step (1)). The photoresist may be patterned into a mask that covers select areas 212 between the anchor regions 221, thereby exposing the surface where pores are desired 213. The non-compliant membrane may then be patterned by etching, e.g., reactive ion etching (RIE), to form the struts 222 and pores 223, e.g., micropores, through the non-compliant membrane in the pattern defined by the mask (FIG. 2, step (2)).

The backside of the based substrate 240 may then be patterned to remove the base substrate material over the area of the window using front-to-back alignment and etching, e.g., deep reactive ion etching (DRIE) (FIG. 2, step (3)). After opening the window area, the sacrificial layer 230 may be removed, e.g., using hydrofluoric acid (FIG. 2, step (4)), thereby opening the path of the pores 223 through the front and back sides of the non-compliant membrane 220. The resulting non-compliant, microporous membrane 220 may be provided supported by the base substrate 240 as a non-compliant, microporous membrane unit 200.

Figure 3B:
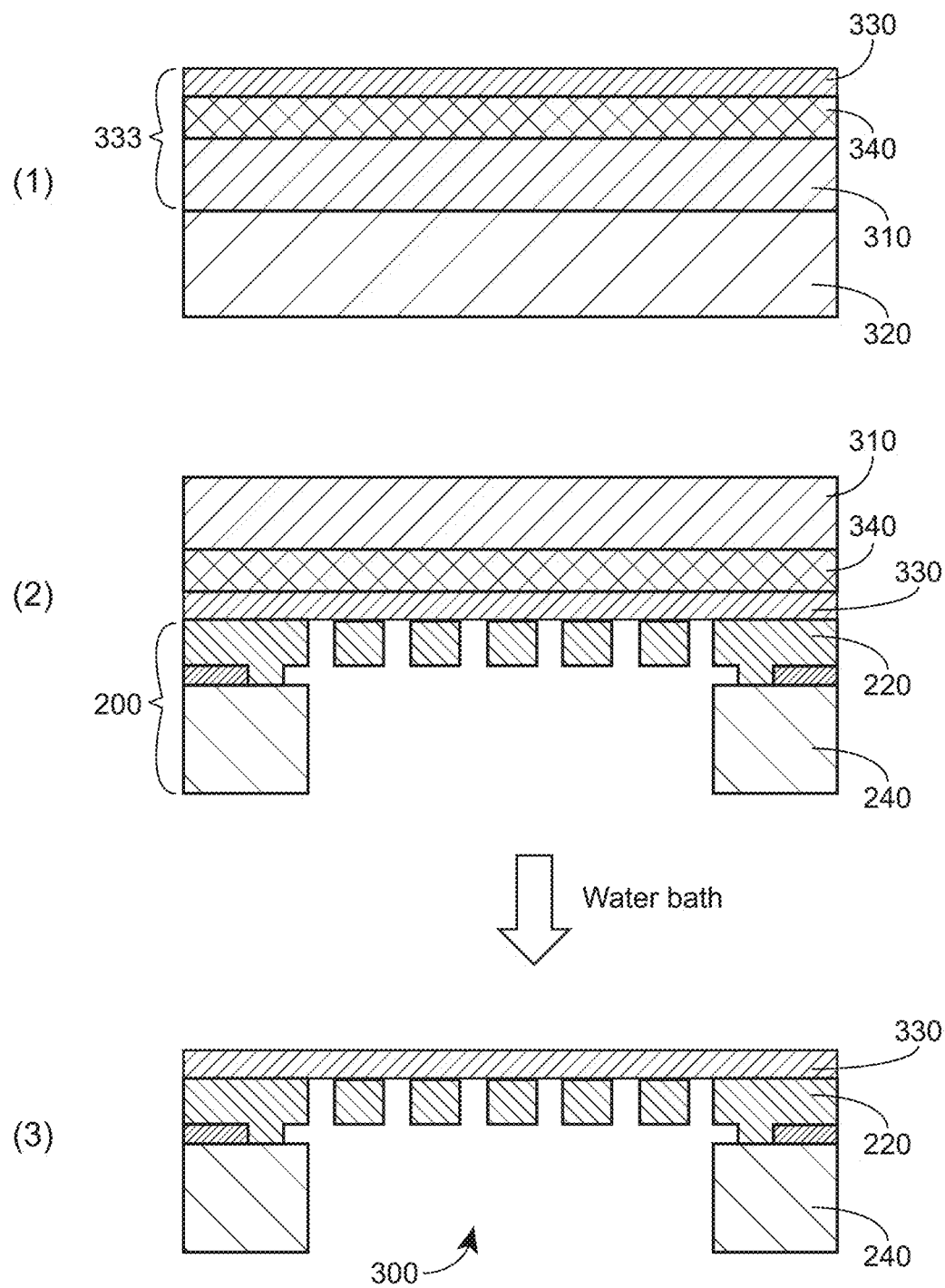
Figure 3C:
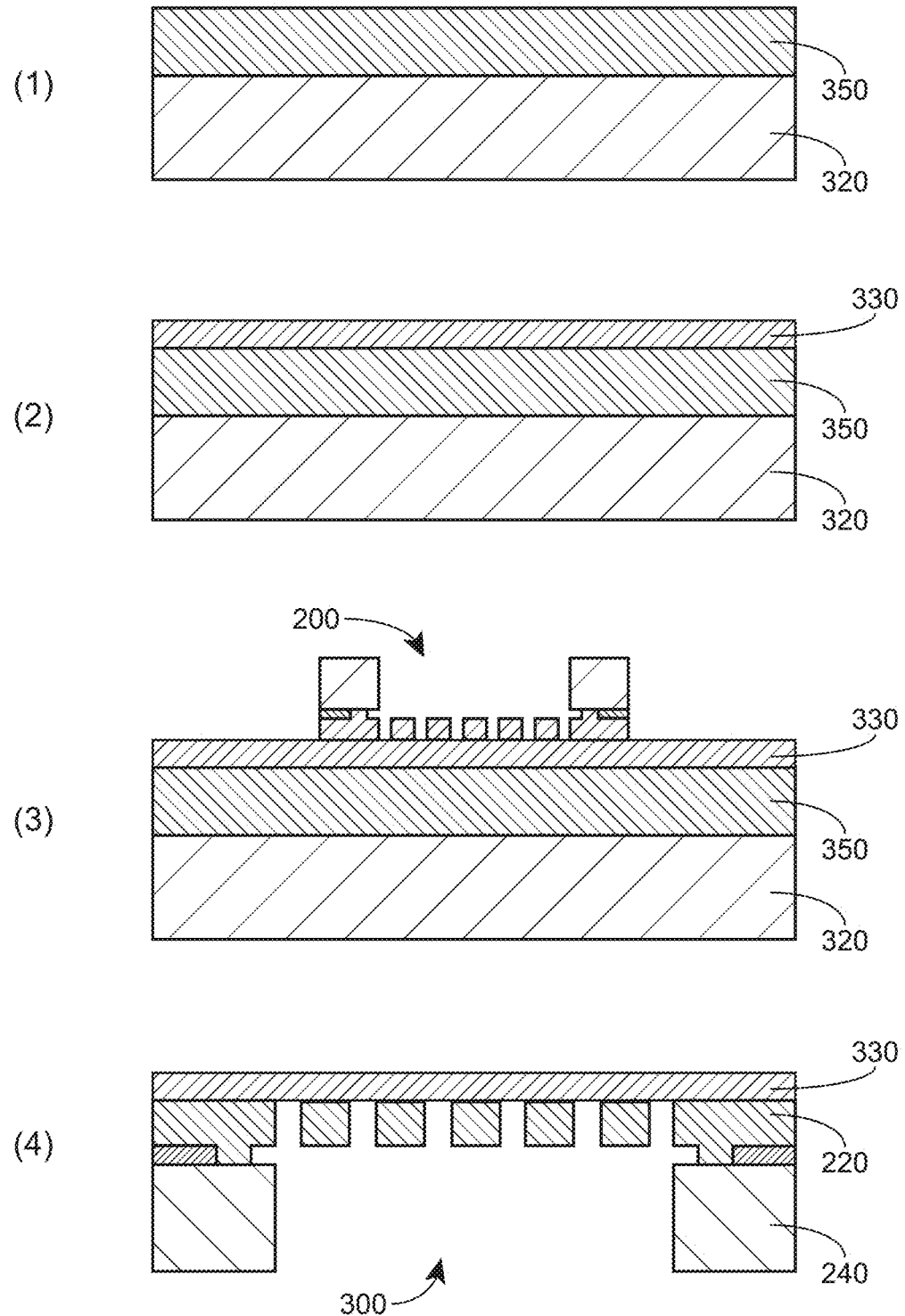

With reference to FIGS. 3A-3C, processes for coating a non-compliant, porous membrane 220 with a non-porous, gas-permeable, polymeric membrane 330 to fabricate a gas exchange composite membrane 300 are provided. In an implementation of the coating process, a transitory supporting membrane 310, e.g., a polydimethylsiloxane (PDMS) supporting membrane, is deposited on a surface of a support substrate 320, e.g., a silicon wafer, that has been surface-treated, e.g., silanized, to render the supporting membrane detachable from the support substrate without significantly deforming the transitory supporting membrane (FIG. 3A, step (1)). For a PDMS supporting membrane, the surface of the support substrate may be treated to make the surface sufficiently hydrophobic to prevent adhesion of the transitory supporting membrane to the support substrate.

Then, a non-porous, gas-permeable, polymeric membrane 330, e.g., a PDMS membrane, is deposited over the transitory supporting membrane 310 (FIG. 3A, step (2)), thereby forming a two-layer, transfer membrane 332, having a top surface formed by the polymeric membrane and the bottom surface formed by the transitory supporting membrane. Before coating the transitory supporting membrane with the polymeric membrane, the exposed surface of the transitory supporting membrane, i.e., the surface of the transitory supporting membrane opposite the surface in contact with the support substrate 320, may be surface treated, e.g., silanized, to render the polymeric membrane detachable from the transitory supporting membrane without significantly deforming the polymeric membrane. In the case that a PDMS polymeric membrane is disposed on the surface of a PDMS supporting membrane, the surface of the transitory supporting membrane may be treated, e.g., by silanization, to make the surface sufficiently hydrophobic to prevent adhesion of the transitory supporting membrane to the polymeric membrane. The transitory supporting membrane may be thicker than the polymeric membrane.

The transfer membrane 332 may then be detached from the support substrate 320 (FIG. 3A, step (3)) using mechanical force, e.g., by peeling. Then the top surface of the transfer membrane, i.e., the exposed surface of the polymeric membrane 330 opposite the surface that is in contact with the transitory supporting membrane 310, is bonded to the top surface of the non-compliant membrane 220, i.e., the surface of the of the membrane opposite the surface that is attached to the base substrate 240 of the non-compliant microporous membrane unit 200 (FIG. 3A, step (4)). In order to bond the polymeric membrane to the non-compliant membrane, the top surface of the transfer membrane and the top surface of the non-compliant membrane may be surface-treated, e.g., exposed to oxygen plasma, before contacting the two top surfaces with each other. An amount of a liquid, e.g., water or isopropyl alcohol, may be spread across the interface between the two top surfaces to promote bonding and prevent air bubble from forming between the layers.

After bonding, the polymeric membrane 330 is detached from the transitory supporting membrane 310 (FIG. 3A, step (4)) by, e.g., peeling the transitory supporting membrane along a direction substantially parallel to the top surface of the non-compliant membrane 220, thereby obtaining a composite membrane 300.

In another implementation of a process for coating a non-compliant, porous membrane 220 with a non-porous, gas-permeable, polymeric membrane 330 to fabricate a composite membrane 300 (FIG. 3B), a transitory supporting membrane 310, e.g., a polydimethylsiloxane (PDMS) supporting membrane, is deposited on a surface of a support substrate 320, e.g., a silicon wafer, that has been surface-treated, e.g., silanized, to render the transitory supporting membrane detachable from the support substrate without significantly deforming the transitory supporting membrane (FIG. 3B, step (1)). For a PDMS supporting membrane, the surface of the support substrate may be treated, e.g., exposed to oxygen plasma, to make the surface sufficiently hydrophilic to allow for deposition of a water-soluble polymer membrane 340.

Then, a water-soluble polymer membrane 340, e.g., a polyvinyl alcohol (PVA) membrane, is deposited over the transitory supporting membrane 310, followed by a non-porous, gas-permeable, polymeric membrane 330, e.g., a PDMS membrane (FIG. 3B, step (1)), thereby forming a three-layer transfer membrane 333, having a top surface formed by the polymeric membrane, the bottom surface formed by the transitory supporting membrane and the water-soluble polymer membrane interposed between the polymeric and transitory supporting membranes.

The transfer membrane 333 may then be detached from the support substrate 320 (FIG. 3B, step (2)) using mechanical force, e.g., by peeling. Then the top surface of the transfer membrane, i.e., the exposed surface of the polymeric membrane 330 opposite the surface that is in contact with the water-soluble polymer membrane 340, is bonded to the top surface of the non-compliant membrane 220, i.e., the surface of the of the non-compliant membrane opposite the surface that is attached to the base substrate 240 of the non-compliant microporous membrane unit 200 (FIG. 3B, step (2)). In order to bond the polymeric membrane to the non-compliant membrane, the top surface of the transfer membrane and the top surface of the non-compliant membrane 220 may be surface-treated, e.g., exposed to oxygen plasma, before contacting the two top surfaces with each other. An amount of a volatile liquid, e.g., isopropyl alcohol, may be spread across the interface between the two top surfaces to promote bonding.

After bonding, the polymeric membrane 330 is detached from the transitory supporting membrane 310 by dissolving the water-soluble polymer membrane 340 by, e.g., exposing the water-soluble polymer membrane to water, thereby obtaining a composite membrane 300 (FIG. 3B, step (3)).

Also provided herein is another process a process for coating a non-compliant, porous membrane component 200 with a non-porous, gas-permeable, polymeric membrane 330 to fabricate a composite membrane 300 (FIG. 3C). Here, a transitory dissolvable film 350, e.g., a film of SU-8 photoresist, is deposited on a surface of a support substrate 320, e.g., a silicon wafer (FIG. 3C, step (1)). The SU-8 may be spin-coated onto the silicon wafer and the coated silicon wafer baked to form the film.

Following deposition of the transitory dissolvable film 350, a non-porous, gas-permeable, polymeric membrane 330, e.g., a PDMS membrane, is deposited over the dissolvable film 350, thereby forming a two-layer membrane on the support substrate 320 (FIG. 3C, step (2)).

Then the top surface of the two-layer membrane, i.e., the exposed surface of the polymeric membrane 330 opposite the surface that is in contact with the transitory dissolvable film 350, is bonded to the top surface of the non-compliant membrane 220, i.e., the surface of the of the non-compliant membrane opposite the surface that is attached to the base substrate 240 of the non-compliant microporous membrane unit 200 (FIG. 3C, step (3)). In order to bond the polymeric membrane to the non-compliant membrane, the top surface of the two-layer membrane and the top surface of the non-compliant membrane may be surface-treated, e.g., exposed to oxygen plasma, before contacting the two top surfaces with each other. An amount of a volatile liquid, e.g., isopropyl alcohol, may be spread across the interface between the two top surfaces to promote bonding.

After bonding, the polymeric membrane 330 is detached from the support substrate 320 by dissolving the transitory dissolvable film 350 by, e.g., exposing the dissolvable film to a solvent, such as acetone, thereby obtaining a composite membrane 300 (FIG. 3C, step (4)).

In some embodiments, the method may further include functionalizing the first surface of the non-porous, gas permeable membrane, e.g., to reduce fouling or coagulation of blood that comes into contact with the first surface, and/or to enhance diffusion of gas from the blood across the membrane. Any suitable functionality may be provided to the first surface using any suitable method. In some cases, the first surface is functionalized with polyethylene glycol (PEG), perfluorocarbon, heparin or carbonic anhydrase. Functionalizing a surface with perfluorocarbon is described in, e.g., Leslie, Daniel C., et al. "A bioinspired omniphobic surface coating on medical devices prevents thrombosis and biofouling." *Nature biotechnology* (2014); functionalizing a surface with PEG is described in, e.g., U.S. Pat. No. 7,695,775; U.S. App. Pub. No. 20060093836; and PCT Pub. No. 2003/102133; functionalizing a surface with heparin is described in, e.g., PCT Pub. No. 2005/118018, all of which are incorporated herein by reference.

The sacrificial layer 230 may have any suitable thickness ("a"). In some cases, the sacrificial layer has a thickness of 0.1 µm or more, e.g., 0.2 µm or more, 0.5 µm or more, 0.75 µm or more, including 1.0 µm or more, and has a thickness of 5.0 µm or less, e.g., 4.0 µm or less, 3.0 µm or less, including 2.0 µm or less. In some cases, the sacrificial layer has a thickness in the range of 0.1 to 5.0 µm, e.g., 0.2 to 4.0 µm 0.5 to 3.0 µm, including 0.75 to 2.0 µm.

The base substrate 240 may have any suitable thickness ("c"). In some embodiments, the base substrate has a thickness of 10 µm or more, e.g., 50 µm or more, 100 µm or more, 200 µm or more, 300 µm or more, including 400 µm or more, and has a thickness of 1,000 µm or less, e.g., 800 µm or less, 600 µm or less, including 500 µm or less. In some cases, the base substrate has a thickness in the range of 10 to 1,000 µm, e.g., 50 to 800 µm, 100 to 600 µm, including 200 to 600 µm.

The transitory supporting membrane 310, may have any suitable thickness ("g"). In certain embodiments, the transitory supporting membrane has a thickness of 0.1 mm or more, e.g., 0.2 mm or more, 0.5 mm or more, 0.75 mm or more, including 1.0 mm or more, and has a thickness of 10 mm or less, e.g., 8.0 mm or less, 6.0 mm or less, 4.0 mm or less, including 3.0 mm or less. In certain embodiments, the transitory supporting membrane has a thickness in the range of 0.1 to 10 mm, e.g., 0.2 to 8.0 mm, 0.5 to 6.0 mm, including 0.75 to 6.0 mm.

The various membranes and films used in the present method may be deposited onto a surface using any suitable method. Suitable methods include, but are not limited to, spin coating, screen printing, spray coating, solvent casting, chemical vapor deposition, and plasma deposition. Coating a surface may further include any suitable curing and/or polymerization steps, e.g., heat curing, ultra-violet (UV) cross-linking, chemical cross-linking, etc.

Blood Oxygenation Devices and Systems

Figure 20:
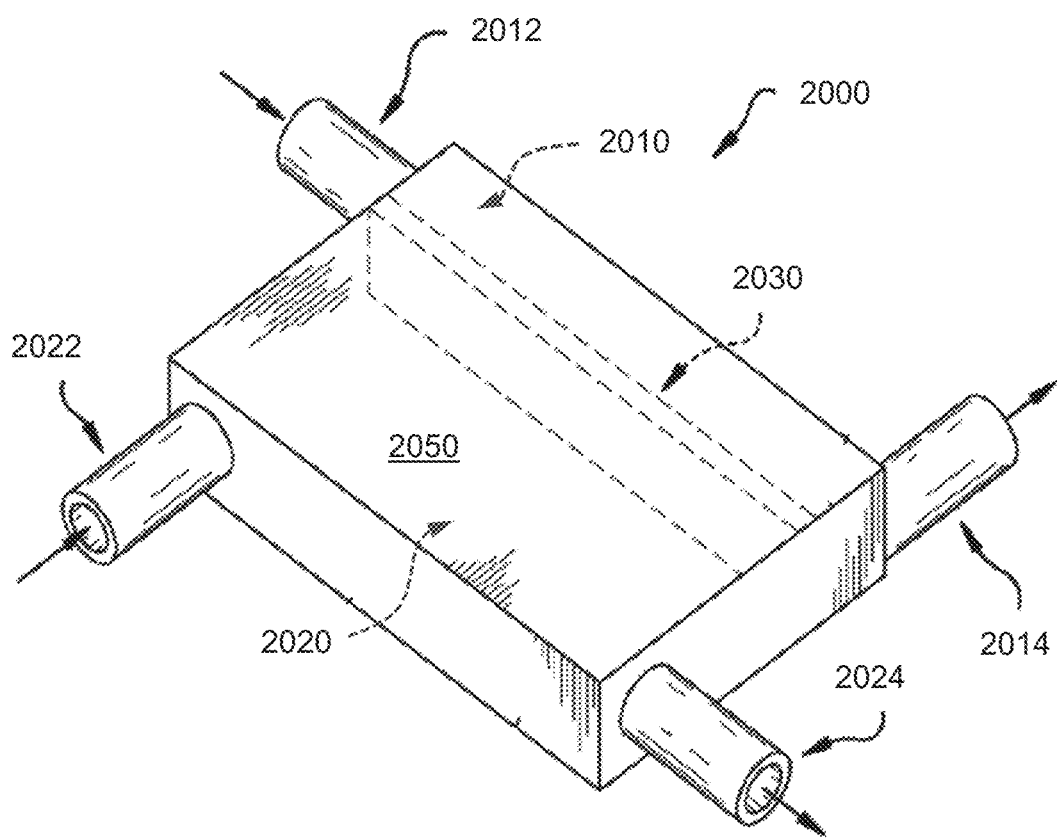
FIG. 20 is a diagram showing a blood oxygenating device, according to embodiments of the present disclosure.

The present disclosure also provides a device for blood oxygenation, that includes a gas exchange composite membrane as described herein (FIG. 20). The blood oxygenation device 2000 may include a blood channel 2010 having an inlet 2012 at a first end and an outlet 2014 at a second end of the blood channel, as well as a gas channel 2020 having an inlet 2022 at a first end and an outlet 2024 at a second end of the gas channel. The gas exchange composite membrane 2030 may be positioned between the blood channel and the gas channel so as to form a gas-permeable barrier between the blood channel and the gas channel, where the polymeric membrane of the composite membrane contacts the blood flowing through the blood channel, and the microporous membrane of the composite membrane contacts the gas flowing through the gas channel (see also FIG. 5). In general terms, deoxygenated blood entering the inlet of the blood channel can be oxygenated by oxygen diffusing from the gas in the gas channel through the composite membrane, as the blood progresses along the composite membrane toward the outlet of the blood channel. Carbon dioxide in the deoxygenated blood entering the inlet of the blood channel may also diffuse through the composite membrane from the blood to the gas in the gas channel, as the blood progresses along the composite membrane toward the outlet of the blood channel. Thus, blood exiting from the blood channel outlet may contain more oxygen and less carbon dioxide than the blood entering the blood channel at the inlet.

In some cases, the device contains two gas exchange composite membranes and two gas channels, where the gas exchange composite membranes flank two sides of the blood channel and a gas channel is provided for each composite membrane.

The blood channel may have any suitable cross-section, where the cross-section is defined by a plane perpendicular to the average direction of flow of the blood flowing through the blood channel. In some cases, the cross-section is substantially circular, oval, rectangular, square, triangular, etc. Where the cross-section is rectangular, the width of the rectangle may be any suitable length. In some cases, the blood channel has a cross-sectional width, along the region that overlaps with a gas diffusion window of a gas exchange composite membrane, of 0.5 mm or more, e.g., 1.0 mm or more, 5.0 mm or more, 10 mm or more, 50 mm or more, including 100 mm or more, and has a cross-sectional width of 300 mm or less, e.g., 250 mm or less, 150 mm or less, 100 mm or less, including 90 mm or less. In some cases, the blood channel has a cross-sectional width, along the region that overlaps with a gas diffusion window of a gas exchange composite membrane, in the range of 0.5 to 300 mm, e.g., 1.0 to 250 mm, 5.0 to 250 mm, including 5.0 to 150 mm. The height of the rectangle may be any suitable height. In some cases, the blood channel has a cross-sectional width of 0.01 mm or more, e.g., 0.05 mm or more, 0.1 mm or more, 0.15 mm or more, 0.2 mm or more, including 0.5 mm or more, and has a cross-sectional height of 2.0 mm or less, e.g., 1.7 mm or less, 1.5 mm or less, 1.3 mm or less, including 1.0 mm or less. In some cases, the blood channel has a cross-sectional height in the range of 0.01 to 2.0 mm, e.g., 0.05 to 1.7 mm, 0.1 to 1.5 mm, 0.15 to 1.3 mm, including 0.15 to 1.0 mm. The ratio of width to height of the blood channel, along the region that overlaps with a gas diffusion window of a gas exchange composite membrane, may be any suitable ratio. In some cases, the ratio of width to height of the blood channel is 10 or more, e.g., 20 or more, 50 or more, 100 or more, 200 or more, including 500 or more, and is 1,000 or less, e.g., 750 or less, 600 or less, including 400 or less. In some cases, the ratio of width to height of the blood channel is in the range of 10 to 1,000, e.g., 20 to 750, 50 to 600, including 100 to 400.

The length of the blood channel, from the first end to the second end of the blood channel, may be any suitable length. In some cases, the length of the blood channel is 1.0 mm or more, e.g., 5.0 mm or more, 10 mm or more, 50 mm or more, 100 mm or more, including 200 mm or more and is 300 mm or less, e.g., 280 mm or less, including 260 mm or less. In some cases, the length of the blood channel is in the range of 1.0 to 300 mm, e.g., 1.0 to 280 mm, 5.0 mm to 280 mm, including 5.0 mm to 260 mm.

The total area of the gas diffusion window of the blood oxygenation device may vary, and, if more than one gas exchange composite membranes are present, may be the combined area of the gas diffusion windows of all of the gas exchange composite membranes. The total area of the gas diffusion window of the blood oxygenation device may be 1.0 $mm^2$ or more, e.g., 10 $mm^2$ or more, 100 $mm^2$ or more, 1,000 $mm^2$ or more, 10,000 $mm^2$ or more, including 0.1 $m^2$ or more, and may be 0.5 $m^2$ or less, e.g., 0.3 $m^2$ or less, 0.1 $m^2$ or less, 10,000 $mm^2$ or less, including 1,000 $mm^2$ or less. In some cases, the total area of the gas diffusion window of the blood oxygenation device may be in the range of 1.0 $mm^2$ to 0.5 $m^2$, e.g., 10 $mm^2$ to 0.3 $m^2$, including 100 $mm^2$ to 0.3 $m^2$.

The total volume of the blood channel may vary, and may be 1.0 $mm^3$ or more, e.g., 10.0 $mm^3$ or more, 100 $mm^3$ or more, 1,000 $mm^3$ or more, 10,000 $mm^3$ or more, including 0.01 $m^3$ or more, and may be 1.5 $m^3$ or less, e.g., 1.0 $m^3$ or less, 0.5 $m^3$ or less, 0.3 $m^3$ or less, including 0.1 $m^3$ or less. In some embodiments, the volume of the blood channel may be in the range of 1 $mm^3$ to 1.5 $m^3$, e.g., 10 $mm^3$ to 1.0 $m^3$, 100 $mm^3$ to 0.5 $m^3$, 1,000 $mm^3$ to 0.5 $m^3$, including 10,000 $mm^3$ to 0.3 $m^3$.

The average direction of the flow of blood through blood channel and average direction of the flow of the gas through the gas channel may be different by any suitable angle. In some cases, the average direction of the flow of blood through blood channel and average direction of the flow of the gas through the gas channel is different by a range of 0° to 10°, 10° to 20°, 20° to 30°, 30° to 40°, 40° to 50°, 50° to 60°, 60° to 70°, or 80° to 90°. In some cases, the average direction of the flow of blood through blood channel is substantially perpendicular to the average direction of the flow of the gas through the gas channel. In some cases, the average direction of the flow of blood through blood channel is substantially parallel to the average direction of the flow of the gas through the gas channel.

In some cases, the inlet and/or outlet has the same width as the width of the blood channel along the region that overlaps with a gas diffusion window of a gas exchange composite membrane. In some cases, the inlet and/or outlet has a different width as the width of the blood channel along the region that overlaps with a gas diffusion window of a gas exchange composite membrane. In some cases, the blood channel may include a channel whose width tapers between an inlet and/or outlet that is narrower than the cross-sectional width of the blood channel along the region that overlaps with a gas diffusion window of a gas exchange composite membrane.

The blood channel, e.g., the portions of the blood channel that is not formed by the gas exchange composite membrane, may be formed using any suitable material. In some cases, the blood channel is a polymeric channel or a metal channel. In some cases, the blood channel is a polycarbonate, polyurethane or a silicone polymer channel. In some cases, the blood channel is made of PDMS. In some embodiments, the blood channel is made of a metal alloy, e.g., a titanium alloy.

In some cases, one or more surfaces of the blood channel are functionalized in any suitable manner to, e.g., reduce coagulation of blood that comes into contact with the channel surface. In some cases, a channel surface is functionalized with polyethylene glycol (PEG).

The gas channel, e.g., the portions of the gas channel that is not formed by the gas exchange composite membrane, may be formed using any suitable material. In some cases, the gas channel is a polymeric channel or a metal channel. In some cases, the gas channel is a polycarbonate, polyurethane, polyester or a silicone polymer channel. In some cases, the gas channel is made of PDMS or acrylic. In some embodiments, the gas channel is made of a metal alloy, e.g., a titanium alloy.

In some embodiments, the blood oxygenation device may be a stackable device. Thus, in some cases, the blood oxygenation device may include a housing with substantially flat outer surfaces to allow stacking of two or more similar blood oxygenation devices on top of each other.

Also provided herein is a system for exchanging gas with blood, e.g., venous blood from a subject in need of blood oxygenation support, to oxygenate the blood. The system may include an extracorporeal blood circuit that includes a peristaltic pump and one or more blood oxygenation devices of the present disclosure. The system may be configured such that the peristaltic pump pumps blood, e.g., deoxygenated blood, such as venous blood, from the subject to the blood oxygenation devices and pumps back oxygenated blood into the subject's circulatory system. Thus, the system may be a closed circuit configured to receive venous blood, e.g., from the vena cavae, and to return oxygenated blood to the right atrium. The system can include a gas supply unit that provides a source of an appropriate gas, e.g., a gas containing a suitable amount of oxygen, to the blood oxygenation devices through a gas conduit, e.g., tubing.

The system may further include any other suitable devices, e.g., monitoring devices and gauges, valves, electronic control units, etc. Monitoring devices may include blood pressure gauges, blood flow meters, blood gas analyzers, such as a hemoximeter, etc. The blood gas analyzer may be an analyzer for oxygen and/or carbon dioxide. Other suitable monitoring devices include blood monitoring devices for sulfur dioxide and/or bicarbonate content. In some cases, the present system includes monitoring devices for the gas, including, but not limited to, gas content analyzer (e.g., carbon monoxide sensor) or flow meters. The system may also include other blood oxygenation devices that are known in the art.

In some cases, the system includes a source of anticoagulants, e.g., heparin. The heparin source may be any suitable heparin source. In certain embodiments, the heparin source is a heparin pump, which may be configured to supply heparin to the extracorporeal circuit before the blood enters the oxygenation devices.

In certain embodiments, the components of the system are small enough to be portable. In some cases, the blood oxygenation devices are small enough to be wearable on the subject. Thus the blood oxygenation devices may be configured to be wearable, e.g. include clips, straps, hooks, or any other attachment elements to attach the device to a clothing or body part of the subject.

Methods of Oxygenating Blood

The present disclosure also includes a method of exchanging gas with blood, e.g., venous blood from a subject in need of blood oxygenation support. In general terms, the method may include pumping blood from a circulatory system of a subject to an extracorporeal blood circuit to generate a circulating flow of the blood, e.g., flow of blood out of a suitable vein, through the extracorporeal blood circuit and back into the subject at a suitable point in the circulatory system, e.g., into the right atrium. The extracorporeal blood circuit includes one or more non-circuitous blood channels of one or more blood oxygenating devices, such as the blood oxygenating devices disclosed herein. Thus, a blood-oxygenating device may include, in addition to the blood channel, a gas channel and gas exchange composite membrane(s) configured to exchange gaseous compounds between the blood and the gas across a planar surface separating the blood channel and the gas channel. As the blood channel is non-circuitous, the blood can flow through the channel without being hindered or diverted by an obstruction in the blood channel, for at least 30%, e.g., at least 40%, at least 50% at least 60%, at least 70%, at least 80%, at least 90%, or for substantially the entire length of the blood channel. The planar surface of the gas exchange composite membrane(s) may provide an unhindered, uniform surface along which blood can flow and be oxygenated.

The method further includes flowing a gas containing through the gas channel, where the gas contains any suitable amount (e.g., partial pressure) of gaseous compounds, e.g., oxygen, to provide the appropriate pressure gradient of the gaseous compound across the gas exchange composite membrane(s). The gas may also provide a sink to draw out gaseous compounds, e.g., carbon dioxide, dissolved in the blood.

The passage of the blood through the blood channel of the blood oxygenating device may be controlled by the shape and dimensions of the blood channel cross-section, the shape of the path through blood channel, and the flow rate, such that the shear stress on the flowing blood is controlled. The shape of the blood channel cross-section, e.g., the cross-section of the blood channel in a plane perpendicular to the average direction of flow of the blood, may be any suitable cross section, and in some cases, may be rectangular. The width of the rectangular cross-section, as defined by the edge of the cross-section that is parallel to the gas exchange surface of the gas exchange composite membrane, may be any suitable width. In some cases, the blood channel has a cross-sectional width, along the region that overlaps with the planar surface of the gas exchange composite membrane across which gas exchange occurs, of 0.5 mm or more, e.g., 1.0 mm or more, 5.0 mm or more, 10 mm or more, 50 mm or more, including 100 mm or more, and has a cross-sectional width of 300 mm or less, e.g., 250 mm or less, 150 mm or less, 100 mm or less, including 90 mm or less. In some cases, the blood channel has a cross-sectional width, along the region that overlaps with the planar surface of the gas exchange composite membrane across which gas exchange occurs, in the range of 0.5 to 300 mm, e.g., 1.0 to 250 mm, 5.0 to 250 mm, including 5.0 to 150 mm. The height of the rectangle may be any suitable height. In some cases, the blood channel has a cross-sectional width of 0.01 mm or more, e.g., 0.05 mm or more, 0.1 mm or more, 0.15 mm or more, 0.2 mm or more, including 0.5 mm or more, and has a cross-sectional height of 2.0 mm or less, e.g., 1.7 mm or less, 1.5 mm or less, 1.3 mm or less, including 1.0 mm or less. In some cases, the blood channel has a cross-sectional height in the range of 0.01 to 2.0 mm, e.g., 0.05 to 1.7 mm, 0.1 to 1.5 mm, 0.15 to 1.3 mm, including 0.15 to 1.0 mm. The ratio of width to height of the blood channel, along the region that overlaps with the planar surface of the gas exchange composite membrane across which gas exchange occurs, may be any suitable ratio. In some cases, the ratio of width to height of the blood channel is 10 or more, e.g., 20 or more, 50 or more, 100 or more, 200 or more, including 500 or more, and is 1,000 or less, e.g., 750 or less, 600 or less, including 400 or less. In some cases, the ratio of width to height of the blood channel is in the range of 10 to 1,000, e.g., 20 to 750, 50 to 600, including 100 to 400.

Pumping the blood may include pumping the blood at a suitable flow rate through the extracorporeal blood circuit and/or through a blood oxygenation device. In some cases the flow rate of the blood through the blood oxygenation device is 0.1 ml/min or more, e.g., 0.2 ml/min or more, 0.5 ml/min or more, 1.0 ml/min or more, 2.0 ml/min or more, 5.0 ml/min or more, 10 ml/min or more, 20 ml/min or more, including 50 ml/min or more, and is 100 ml/min or less, 80 ml/min or less, 60 ml/min or less, 40 ml/min or less, 20 ml/min or less, including 10 ml/min or less. In some cases, the blood is pumped through the blood oxygenation device at a flow rate in the range of 0.1 to 100 ml/min, e.g., 0.1 to 60 ml/min, 0.2 to 20 ml/min, including 0.5 to 10 ml/min.

The blood flowing through the blood channel can have any suitable maximum shear stress. In some cases, the blood flowing through the blood channel has a maximum shear stress of 1,000 dyne cm$^{-2}$ or less, e.g., 800 dyne cm$^{-2}$ or less, 500 dyne cm$^{-2}$ or less, 300 dyne cm$^{-2}$ or less, 250 dyne cm$^{-2}$ or less, including 200 dyne cm$^{-2}$ or less.

The gaseous compound, e.g., oxygen, in the flow of gas can have any suitable partial pressure, e.g., partial pressure relative to atmospheric pressure. In some cases, the partial pressure of the gaseous compound in the flow of gas is 10 cmHg or more, e.g., 20 cmHg or more, 50 cmHg or more, 70 cmHg or more, 90 cmHg or more, 100 cmHg or more, including 120 cmHg or more, and is 500 cmHg or less, e.g., 350 cmHg or less, 250 cmHg or less, 150 cmHg or less, including 130 cmHg or less. In some cases, the partial pressure of the gaseous compound in the flow of gas is in the range of 10 to 500 cmHg, e.g., 20 to 350 cmHg, 50 to 250 cmHg, 90 to 250 cmHg, including 100 to 150 cmHg.

The blood oxygenating device(s) may together provide a large surface area for gas exchange. In some cases, the blood oxygenating device(s) collectively provide a gas exchange surface area of 0.1 m$^2$ or more, e.g., 0.2 m$^2$ or more, 0.3 m$^2$ or more, 0.5 m$^2$ or more, 0.7 m$^2$ or more, 1.0 m$^2$ or more, 2.0 m$^2$ or more, 3.0 m$^2$ or more, including 4.0 m$^2$ or more, and provide a gas exchange surface area of 5.0 m$^2$ or less, e.g., 3.5 m$^2$ or less, 2.5 m$^2$ or less, 1.5 m$^2$ or less, including 0.8 or less. In some cases, the blood oxygenating device(s) collectively provide a gas exchange surface area in the range of 0.1 to 5.0 m$^2$, e.g., 0.2 to 3.5 m$^2$, 0.2 to 2.5 m$^2$, 0.5 to 2.5 m$^2$, including 1.0 to 2.5 m$^2$.

The non-circuitous blood channel may provide for a suitable hydraulic pressure drop of the flow of blood before and after the blood oxygenating device. The flow of blood across each of the non-circuitous blood channels can have a hydraulic pressure drop of 100 mmHg or less, e.g., 80 mmHg or less, 60 mmHg or less, 30 mmHg or less, 20 mmHg or less, 15 mmHg or less, 12 mmHg or less, 10 mmHg or less, including 5.0 mmHg or less.

The subject can be any suitable animal subject, e.g., a mammalian subject, such as a human, non-human primate, pig, horse, cow, sheep, dog, cat, mouse, rat, etc. In some cases, the subject is a patient in need of blood oxygenation support, e.g., a patient with an acute respiratory distress or a patient undergoing lung surgery. In some cases, the patient is a patient diagnosed with acute respiratory distress syndrome (ARDS), or chronic obstructive pulmonary disease (COPD). In some cases, the patient is a patient undergoing lung transplantation.

The present method of exchanging gas with blood can be an efficient method of exchanging gas with blood. In some cases, the method provides an oxygen transfer rate between the gas and the blood at each blood oxygenation device of 0.5 mL STP/cmHg/m$^2$/min or more, e.g., 1.0 mL STP/cmHg/m$^2$/min or more, 1.5 mL STP/cmHg/m$^2$/min or more, including 2.0 mL STP/cmHg/m$^2$/min or more, and has an oxygen gas transfer rate of 10 mL STP/cmHg/m$^2$/min or less, e.g., 8.0 mL STP/cmHg/m$^2$/min or less, 6.0 mL STP/cmHg/m$^2$/min or less, 4.0 mL STP/cmHg/m$^2$/min or less, including 3.0 mL STP/cmHg/m$^2$/min or less, at an average blood flow rate in the rage of about 0.1 to about 1.0 mL/min through each blood oxygenation device. In some embodiments, the method provides an oxygen transfer rate between the gas and the blood at each blood oxygenation device in the range of 0.5 to 10 mL STP/cmHg/m$^2$/min, e.g., 1.0 to 8.0 mL STP/cmHg/m$^2$/min, 1.5 to 6.0 mL STP/cmHg/m$^2$/min, including 1.5 to 4.0 mL STP/cmHg/m$^2$/min, at an average blood flow rate in the rage of about 0.1 to about 1.0 mL/min through each blood oxygenation device.

In some cases, the method provides a carbon dioxide transfer rate between the gas and the blood at each blood oxygenation device of 2.0 mL STP/cmHg/m$^2$/min or more, e.g., 2.5 mL STP/cmHg/m$^2$/min or more, 3.0 mL STP/cmHg/m$^2$/min or more, 4.0 mL STP/cmHg/m$^2$/min or more, including 5.0 mL STP/cmHg/m$^2$/min or more, and has a carbon dioxide gas transfer rate of 50 mL STP/cmHg/m$^2$/min or less, e.g., 40 mL STP/cmHg/m$^2$/min or less, 30 mL STP/cmHg/m$^2$/min or less, 20 mL STP/cmHg/m$^2$/min or less, including 10 mL STP/cmHg/m$^2$/min or less, at an average blood flow rate in the rage of about 0.1 to about 1.0 mL/min through each blood oxygenation device. In some embodiments, the method provides a carbon dioxide transfer rate between the gas and the blood at each blood oxygenation device in the range of 2.0 to 50 mL STP/cmHg/m$^2$/min, e.g., 3.0 to 30 mL STP/cmHg/m$^2$/min, 4.0 to 20 mL STP/cmHg/m$^2$/min, including 5.0 to 10 mL STP/cmHg/m$^2$/min, at an average blood flow rate in the rage of about 0.1 to about 1.0 mL/min through each blood oxygenation device.

Kits

Also provided herein are kits that find use in performing methods of gas exchanging blood from a subject in need of blood oxygenation, as described herein. The present kit may include a gas exchange composite membrane of the present disclosure and a housing that includes a blood channel and a gas channel, wherein the housing is configured to receive the gas exchange composite membrane between the blood channel and the gas channel, wherein the gas exchange composite membrane forms a gas permeable barrier between the blood channel and the gas channel.

The present kit may include any other suitable component for performing a method of gas exchanging blood from a subject in need of blood oxygenation, as described herein. In some cases, the present kit includes instructions for using the gas exchange composite membrane in the housing. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Silicon-Supported Extracorporeal Membrane Oxygenation in an Ovine Live Animal Model Methods Membrane Fabrication Silicon micropore membranes (SµMs). SµMs were produced in wafer-scale arrays of 500 nm by 4 µm rectangular slit pores. A 4-inch, 400 µm thick silicon wafer was heated in a wet oxidation furnace for 1 hr at 1050° C. to generate a 1 µm thick thermal oxide film. The oxide layer was patterned with anchor regions to divide the wafer into 60 µm by 240 µm "window" sub regions. A 1 µm thick polysilicon film was then deposited and patterned via photolithography and reactive ion etching (RIE) to define the slit pores (FIG. 2, steps (1) and (2)), with a pore pitch of 500 nm. The backside of the wafer was then patterned to define the same window dimensions using front-to-back alignment and deep reactive ion etching (DRIE) (FIG. 2, step (3)). The wafer was subsequently diced into 1 cm² membranes containing 1500 windows each. Lastly, 49% hydrofluoric acid was used to remove the oxide etch-stop layer and open the slit pores (FIG. 2, step (4)).

FIG. 2. Process flow for fabrication of a silicon micropore membrane (SµM). Cross-section illustrates a single membrane "window" (not to scale). (A) Polysilicon layer is deposited and patterned on top of oxide film. (B) Polysilicon is etched to define 0.5 µm by 4 µm rectangular pores. (C) Backside bulk silicon is etched to open membrane window. (D) Sacrificial oxide layer is etched to open path between pores and backside of membrane.

PDMS coating. SµMs were coated with polydimethylsiloxane (PDMS) using a lift off process derived from Ingber and colleagues (Kim et al., Nature Protocols, 2013, 8:2135). First, a 4-inch silicon wafer was silanized to prevent adhesion to PDMS by exposure to trichloro(1H, 1H, 2H, 2H-perfluoro-octyl)silane (Sigma-Aldrich, St. Louis, Mo., USA) vapor in a vacuum chamber for 36 hours. Sylgard® 184 PDMS (Dow Corning, Midland, Mich.) was then mixed at a monomer to crosslinker ratio of 10:1 and spin-coated onto the silicon wafer at 500 rpm for 20 seconds. The PDMS was heat-cured at 80° C. for 2 hours to form a ~1 mm thick film, denoted as the "thick PDMS" layer (FIG. 3A, step (1), 310). The silanization process was repeated to passivate the thick PDMS.

A second PDMS layer was then prepared, using a 10:1 monomer:crosslinker ratio diluted with 50% hexanes (Sigma-Aldrich, St. Louis, Mo., USA) by mass to reduce the mixture viscosity. The PDMS mixture was spin-coated atop the thick PDMS wafer at 6000 rpm for 5 minutes, then heat-cured at 80° C. for 2 hours to form a ~3 µm thick film, denoted as the "thin PDMS" layer (FIG. 3A, step (2), 330). After curing, the thin and thick PDMS layers were peeled from the silicon wafer as one piece (FIG. 3A, step (3)). This allowed the thick PDMS layer to act as a flexible supporting substrate for the thin PDMS, preventing wrinkling of the thin film prior to transfer to the SµM.

FIG. 3A. Process flow for polydimethylsiloxane (PDMS) bonding to SµMs. Cross-section illustrates a single membrane "window" (not to scale). (1) Thick PDMS layer (~1 mm) is spun onto silanized silicon wafer and heat cured. (2) Thick PDMS is silanized and spin coated with hexane-diluted PDMS to define thin PDMS film. (3) Thick and thin PDMS layers are peeled from silicon wafer as single sheet. (4) Thin PDMS layer is plasma-bonded to SµM; thick PDMS is peeled away. (5) Complete PDMS-SµM.

The SµM and PDMS were both exposed to oxygen plasma at 100 W for 10 s. A 5 µL drop of isopropyl alcohol was deposited on the surface of the thin PDMS layer, then the SµM was settled onto the PDMS, ensuring a conformal bond as the alcohol evaporated. The PDMS and SµM were allowed to bond at room temperature for 24 hours. The thick PDMS layer was then removed, peeling away nearly parallel to the SµM surface to minimize out-of-plane stresses on the membrane (FIG. 3A, step (4)), leaving the complete asymmetric membrane unit (FIG. 3A, step (5) and FIG. 4A).

Figure 4A:
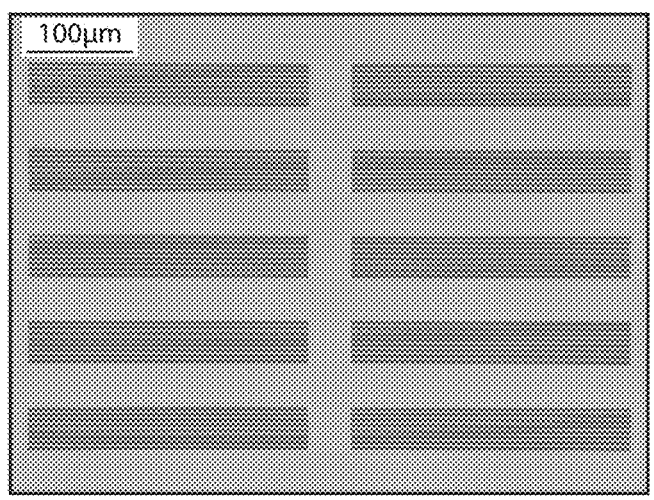
FIGS. 4A-4D are images showing different views of a gas exchange composite membrane, according to embodiments of the present disclosure.

FIG. 4A. Light microscope image of PDMS-SµM.

SµM pore dimensions, membrane polysilicon thickness, and PDMS film thickness were characterized using scanning electron microscopy (SEM).

Membrane Performance Characterization

Membrane pressure loading. Membrane mechanical robustness was experimentally verified by subjecting the complete PDMS-SµMs to leak testing using a bench top hydraulic permeability testing system[14], which is capable of measuring water flux per unit pressure on the order of nanoliters per minute in response to a transmembrane pressure gradient. Water was flowed in contact with the PDMS side of the membrane at a transmembrane pressure of 260 mmHg for 30 min. Any water that passed through fractures or tears in the membrane was collected and measured in a humidified chamber on a mass balance.

Gas diffusion testing. The PDMS-SµMs were tested for gas permeability in a dry bench-top flow cell connected to a pressurized gas supply and a bubble flow meter (Sigma-Aldrich, St. Louis, Mo., USA), similar to a setup used by Burgess et al[15]. The pressurized gas, either oxygen or carbon dioxide, was applied to one side of the membrane to form a transmembrane partial pressure gradient between 700 and 1400 mmHg. As gas diffused across the membrane, it displaced a meniscus of detergent in the bubble flow meter, which allowed direct measurement of the volume of gas transported across the membrane. By measuring the gas flux in the bubble flow meter, gas permeability could be calculated for the PDMS-SµMs as a function of gas flux per unit membrane area.

Blood Gas Transport

Blood channel and sweep gas channel geometry. The blood channel was 3D-printed using PolyJet HD (Solid Concepts, Inc., Valencia, Calif., USA), a urethane-based resin, to define a channel over the PDMS-SµM with dimensions of 1000 µm×800 µm×200 µm (L×W×H), tapering at the inlet and outlet to interface with 1/16" Luer lock tubing connectors. The sweep gas channel was machined from acrylic plastic to form a 3 mm tall chamber over the backside of the PDMS-SµM. The complete device was assembled by compressing a 125 µm thick silicone gasket between the PDMS-SµM and the sweep gas chamber; the stack of components was secured with machines screws. Blood flow rates through the device were chosen to maintain wall shear stress below hemolysis thresholds.

Figure 7A:
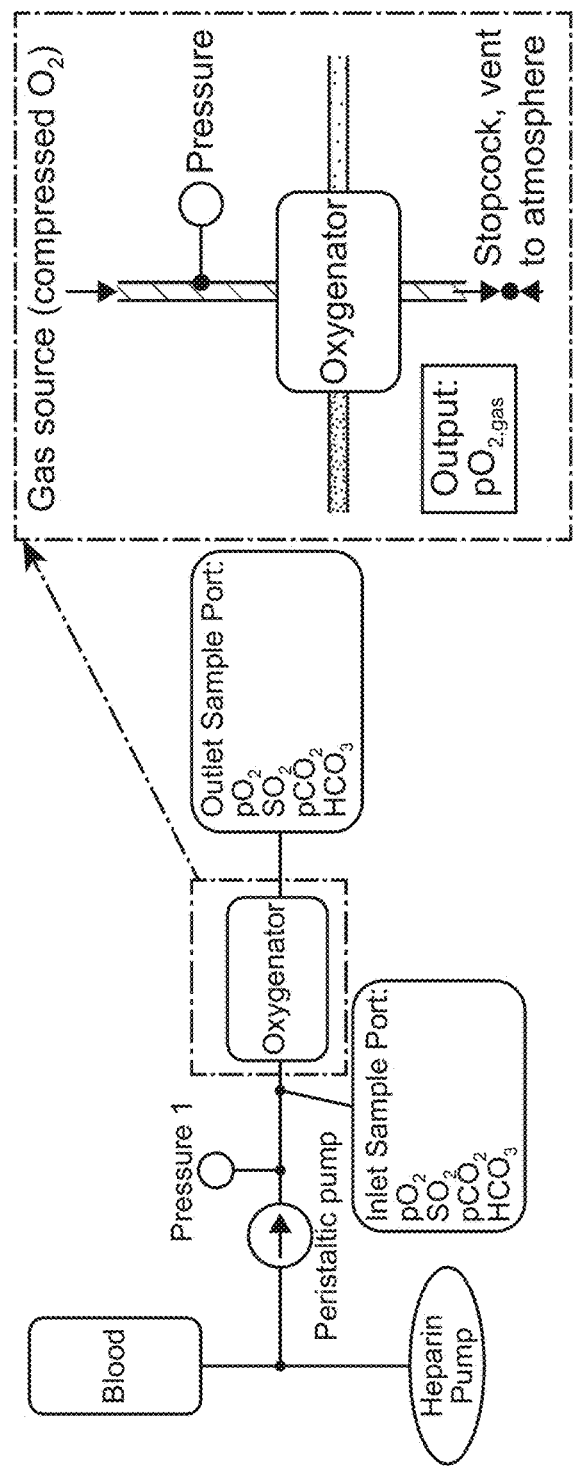
FIGS. 7A and 7B are schematic diagrams showing systems for oxygenating blood using a blood oxygenation device that includes a gas exchange composite membrane, according to embodiments of the present disclosure.

Gas exchange ex vivo. Whole ovine blood was used in a 200 µm blood channel device. The blood was collected in citrate phosphate dextrose adenine (CPDA-1) bags from anesthetized sheep immediately prior to planned termination for an unrelated experiment. Testing was conducted over a 3-hour period. Blood was maintained in a warming bath at 39° C. throughout the experiment and a peristaltic pump (Cole-Parmer, Vernon Hills, Ill., USA) was used to circulate blood through the device with a digital pressure gauge (General Electric Measurement & Control, Billerica, Mass., USA) monitoring blood inflow pressure continuously (FIG. 7A). The blood channel, gas channel, and PDMS-SµM were assembled dry, then primed with 20 Units/mL heparin saline for 15 minutes prior to introduction of blood into the circuit. Pure oxygen sweep gas was supplied to the device at a flow rate of 2.5 L/min, maintaining a sweep pressure of 10 psig. Blood flow rates were set at 0.1, 0.2, 0.5 and 1 mL/min. The order of flow rates was determined using a random number generator, providing for two full cycles of the four flow rates. Three blood samples at each flow rate were collected from both the inlet and outlet, and analyzed at six-minute intervals using an ABL5 blood gas analyzer (Radiometer America, Westlake, Ohio, USA). The analyzer provided pH, pCO2, pO2, SO2, HCO3 and base excess for each sample, allowing membrane exchange to be calculated using Henry's law. The blood gas analyzer was automatically calibrated throughout the experiment. Blood was assessed for gross coagulation after each draw.

FIG. 7A. Schematic of ex vivo gas exchange experiment. Citrated blood maintained at 39 C in water bath was pumped through the oxygenator, with blood samples collected at the oxygenator inlet and outlet in a single-pass manner.

Gas exchange in vivo. For in vivo testing, a similar set-up was utilized (FIG. 7B), the primary difference being the connection of the device inflow and outflow ports to an adult ewe with bilateral saphenous vein catheters (venous inlet right leg used 8 Fr feeding tube; venous return left leg used 050). The animal was sedated with a continuous drip of ketamine (0.3 mg/kg/min), diazepam (0.002 mg/kg/min), and fentanyl (1 µg/kg/hr) for anesthesia and analgesia using an internal jugular vein catheter and hemodynamics were monitored continuously through a femoral arterial line; the ewe was maintained on room air for the duration of the experiment without advanced airway control. Animals were placed on their back on a heated, v-shaped table. Trained veterinary staff placed the saphenous catheters, internal jugular catheter and administered anesthesia. A heparin bolus of 100 Units/kg was given immediately prior to connection of the saphenous catheters to the device and a continuous infusion of heparin at 20 Units/min from a syringe pump (KD Scientific, Holliston, Mass., USA) was used to maintain adequate anticoagulation through the device. At the conclusion of the experiment, the animal was euthanized while sedated using sodium pentobarbital. The experiment protocol was approved by the Institutional Animal Care and Use Committee at the University of California San Francisco.

Figure 7B:
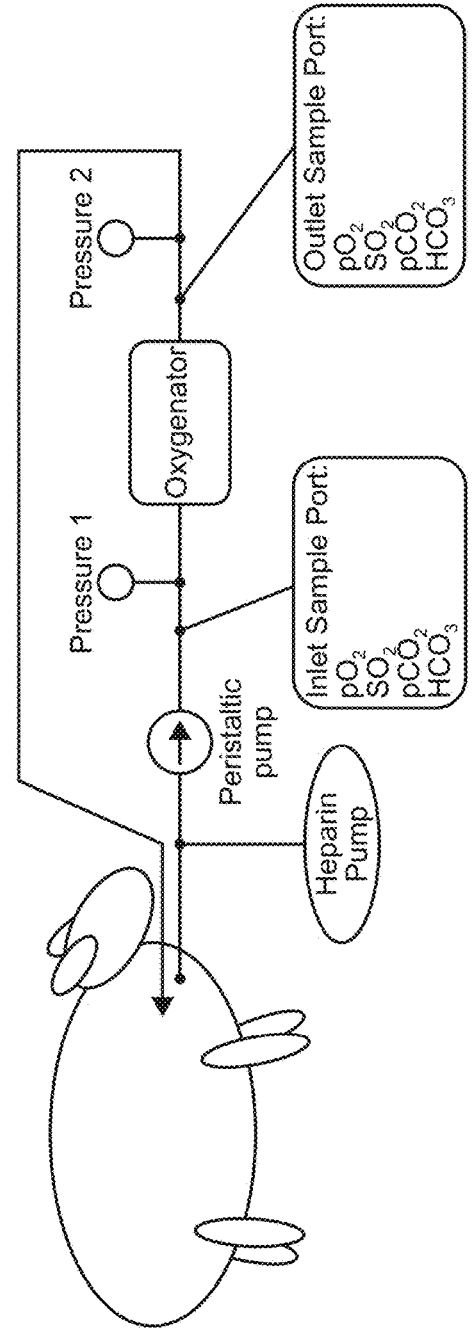

FIG. 7B. Schematic of in vivo gas exchange experiment. Venous blood from an adult ewe was withdrawn by a peristaltic pump and anti-coagulated by an inline heparin infusion pump. Blood samples were collected at the oxygenator inlet and outlet before returning to systemic circulation via a separate venous line.

Results

Membrane Characterization

Figure 4B:
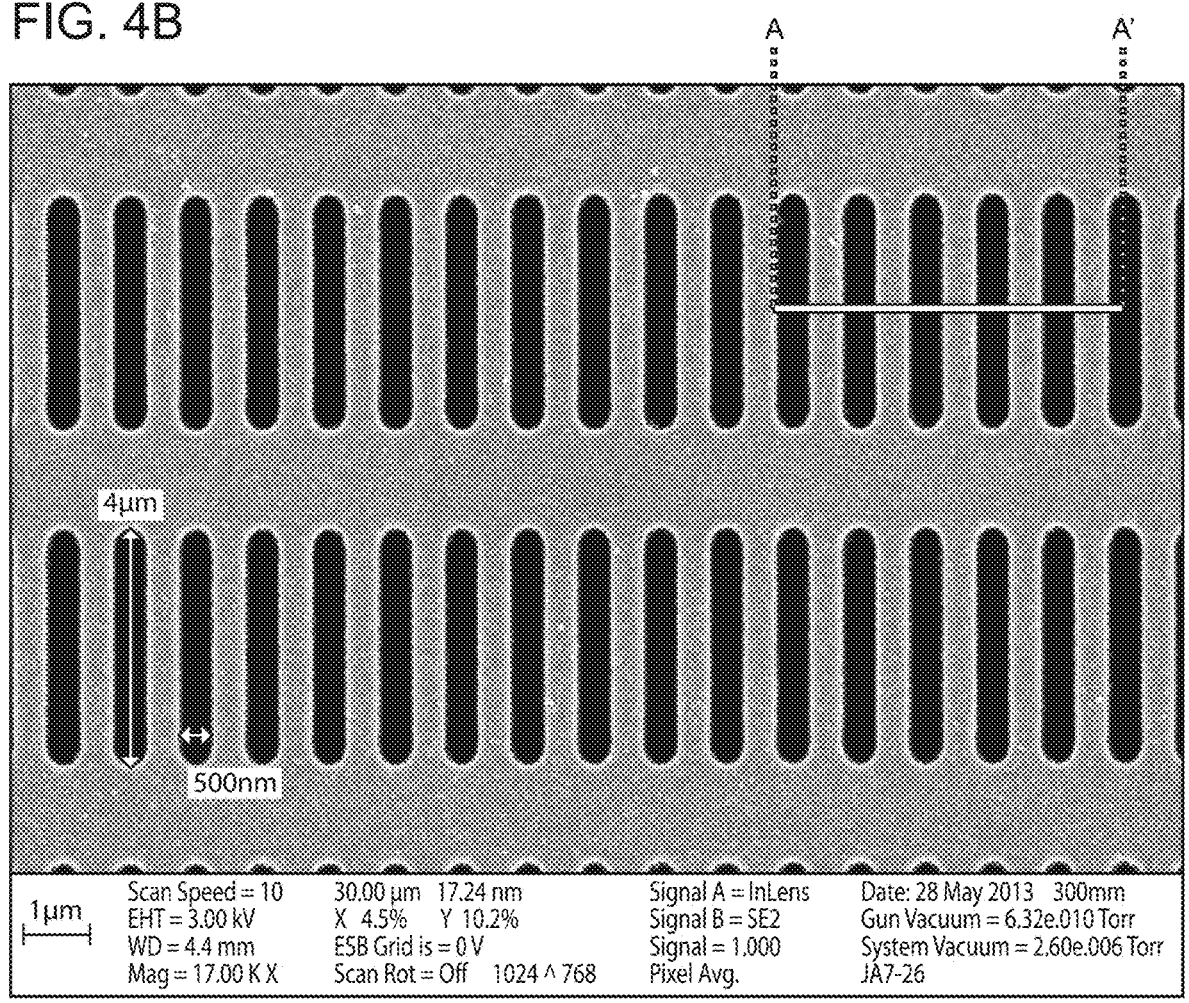
Figure 4C:
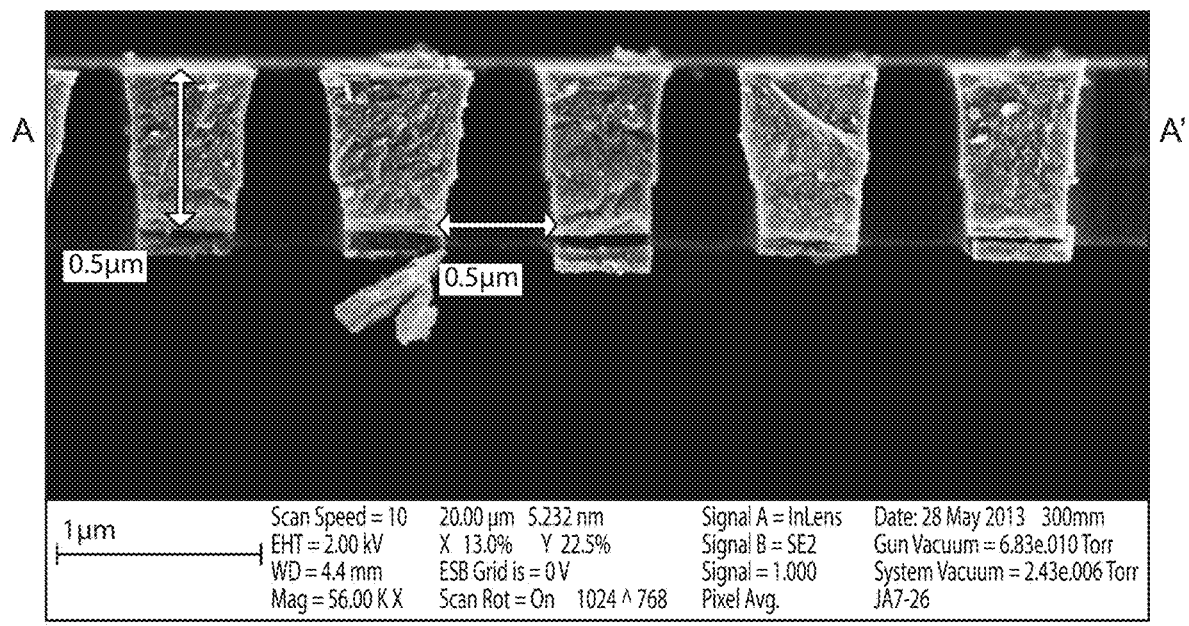
Figure 4D:
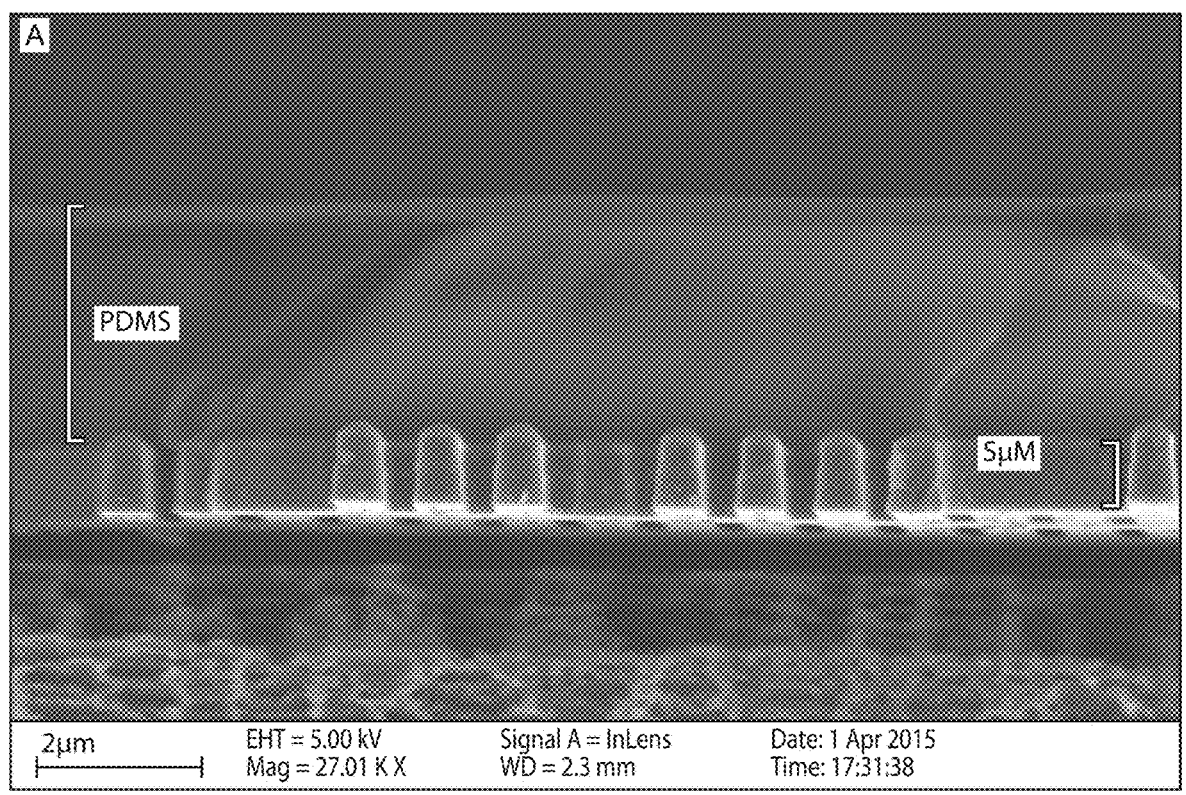

Scanning electron micrographs of the PDMS-SµMs confirmed the presence of a conformal PDMS film with a thickness of 3.25±0.08 µm; the polysilicon support layer of the SµM was measured to be 0.96±0.06 µm thick (FIG. 4D). SµM pore dimensions were 0.48±0.01 µm wide and 3.57±0.01 µm long.

FIG. 4D. Cross section SEM of PDMS-SµM. Blood flows in contact with the PDMS film, while sweep gas flows on the silicon membrane side, diffusing through the PDMS to the blood.

No water flow was detected across the PDMS-SµMs during hydraulic permeability testing, confirming the integrity of the PDMS gas exchange membrane.

Membrane Gas Permeability

Figure 8:
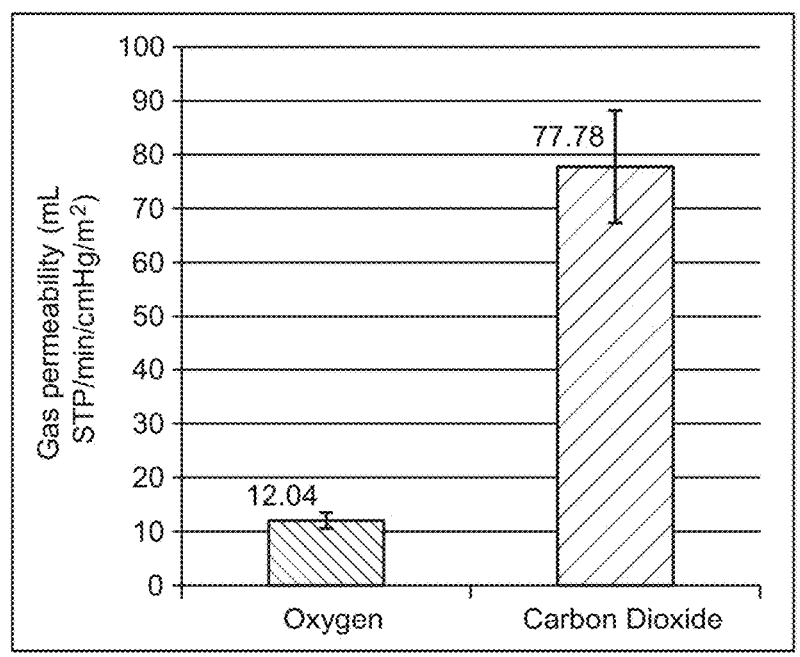
FIG. 8 is a graph showing gas permeability of a gas exchange composite membrane, according to embodiments of the present disclosure.

Collection of 100 µL carbon dioxide and 10 µL oxygen gas permeate was conducted three times for each membrane. The volumes were chosen to allow rapid collection of the target gas before the gas concentration gradient on each side of the membrane became equalized. A set of six PDMS-SµMs were tested, producing gas permeability results of 12.04±1.45 mL STP/min/cmHg/m$^2$ for oxygen and 77.78±10.42 mL STP/min/cmHg/m$^2$ for carbon dioxide (FIG. 8). Two of the most similar PDMS-SµMs were selected for comparative studies between in vivo and ex vivo blood oxygenation experiments. For in vivo testing, the selected membrane had the following permeability: 11.17±1.52 mL STP/min/cmHg/m$^2$ for $O_2$ and 85.07±2.35 mL STP/min/cmHg/m$^2$ for $CO_2$. The membrane selected for ex vivo testing exhibited similar permeability: 11.19±1.81 mL STP/min/cmHg/m$^2$ for $O_2$ and 85.37±14.26 mL STP/min/cmHg/m$^2$ for $CO_2$.

FIG. 8. Membrane permeability to oxygen and carbon dioxide. Transport was measured by diffusion from pure sample gas to room air.

Ovine Ex Vivo Testing

Figure 6A:
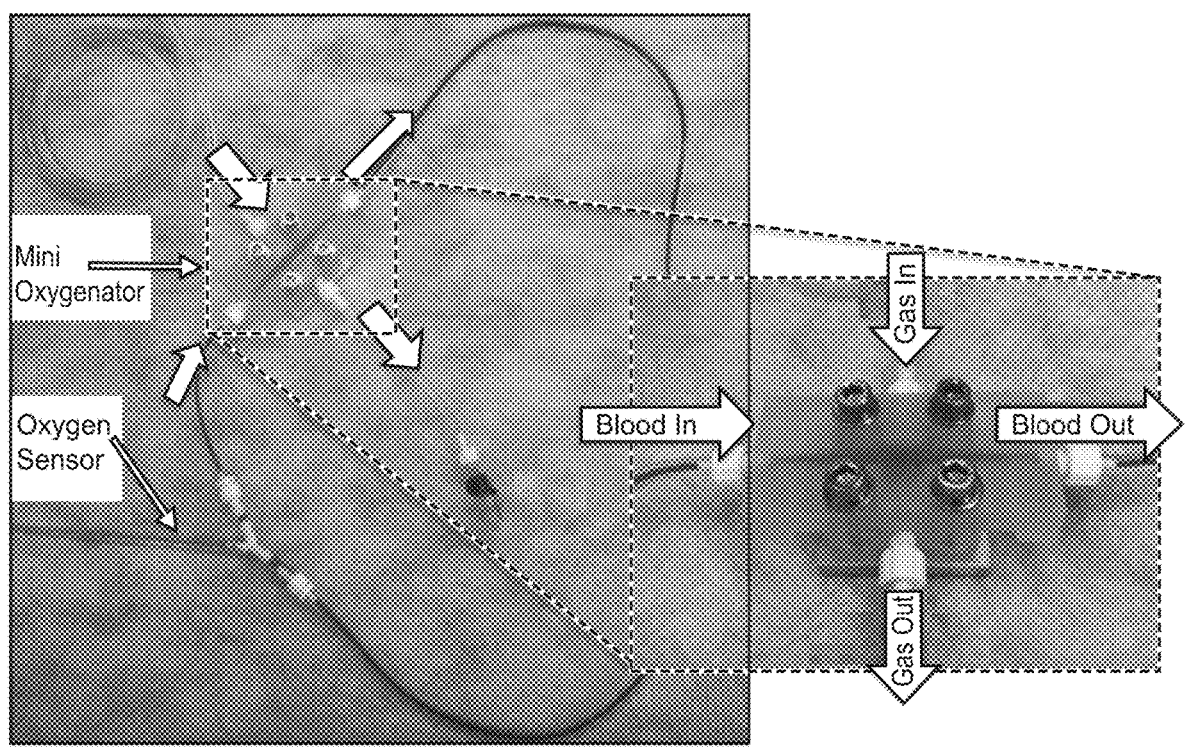
FIGS. 6A and 6B are a collection of images showing a blood oxygenation device that includes a gas exchange composite membrane, according to embodiments of the present disclosure.
Figure 6B:
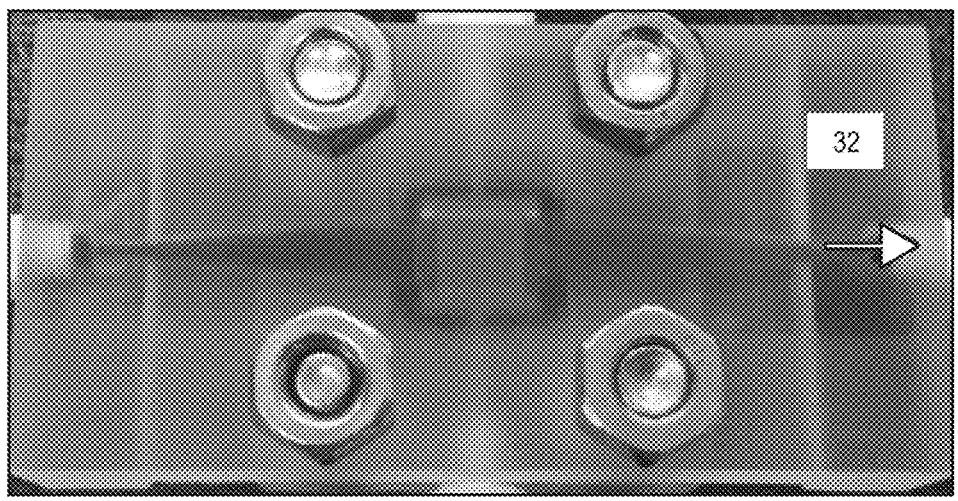

Citrated whole ovine blood was passed in contact with a PDMS-SµM in a 200 µm high channel for 3 hours in a single-pass experiment. Blood pressure drop across the device remained below 5 mmHg (FIG. 9) with a homogeneous blood flow pattern for the duration of the experiment (FIG. 6B). No coagulation was detected in blood drawn from the inlet or outlet sample ports. The pH, $pCO_2$, and $pO_2$ of blood at the inlet sample port remained stable throughout the experiment with pH 6.97±0.12, $pCO_2$ 93.5±3.7 mmHg, and $pO_2$ 40.8±1.7 mmHg.

FIG. 6B. Citrated whole blood flowing through 200 µm high blood channel during ex vivo testing.

Figure 9:
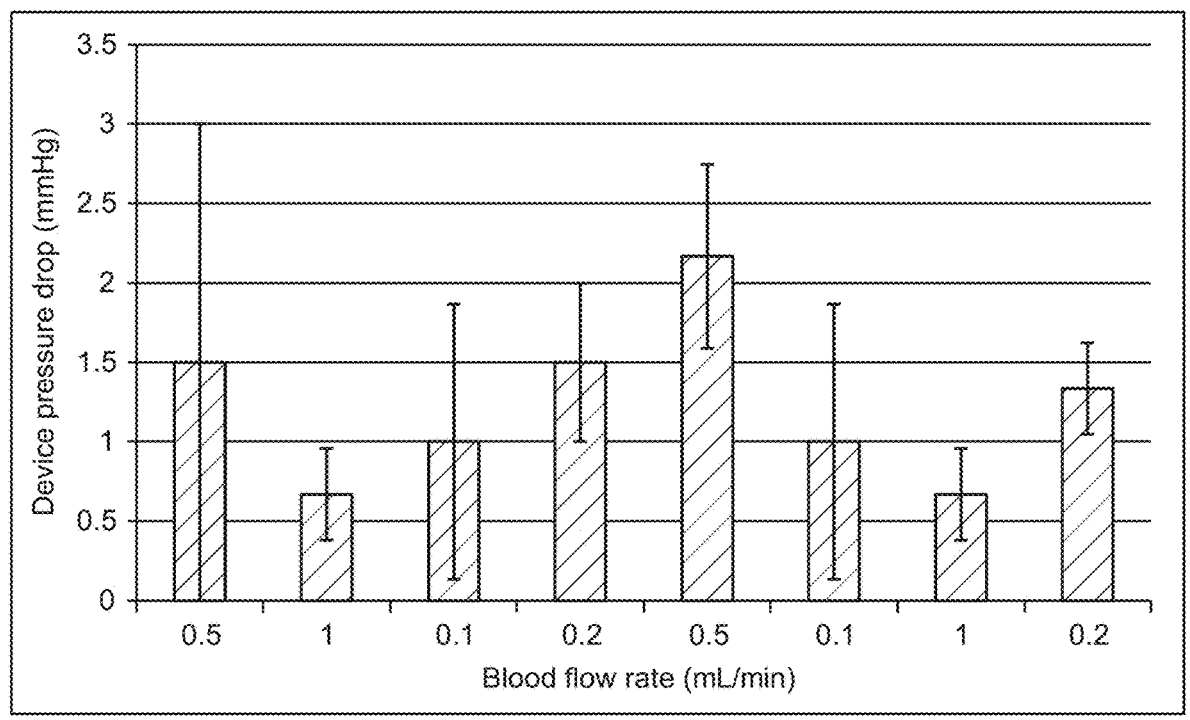
FIG. 9 is a graph showing pressure drop between an inlet and an outlet of blood flowing through a blood oxygenation device that includes a gas exchange composite membrane in ex vivo tests, according to embodiments of the present disclosure.

FIG. 9. Pressure drop between oxygenator inlet and outlet (average±standard deviation) during ex vivo tests. Blood flow rates were cycled twice in random order; results displayed in chronological order from left to right.

Figure 10A:
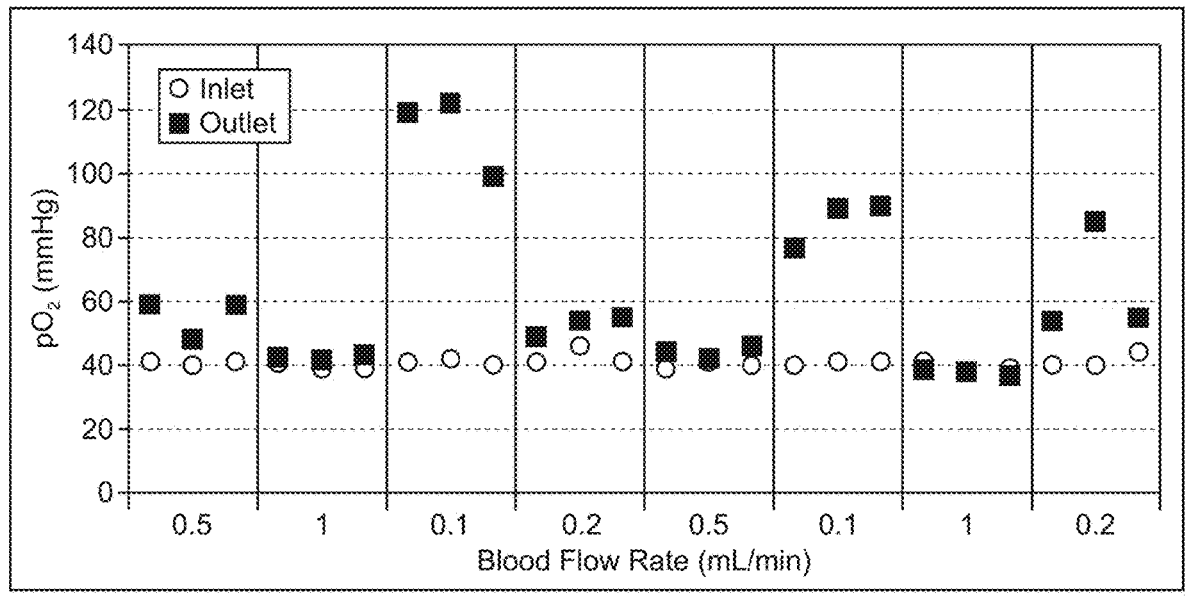
FIGS. 10A and 10B are a collection of graphs showing oxygen partial pressure and oxygen exchange rates, respectively, in blood flowing through a blood oxygenation device that includes a gas exchange composite membrane in ex vivo tests, according to embodiments of the present disclosure.

Significant oxygen exchange was seen at all flow rates except for 1 mL/min (FIG. 10A). The permeability of the PDMS-SµM at each flow rate was variable (FIG. 10B), with a general trend toward decreasing $O_2$ permeability with time independent of flow rate. The initial observed $O_2$ permeability was 5.97±3.13 mL STP/min/cmHg/m2. $CO_2$ permeability at the onset of the experiment was 19.77±12.30 mL STP/min/cmHg/m2, but no appreciable exchange was detectable thereafter (FIGS. 11A-11B).

Figure 10B:
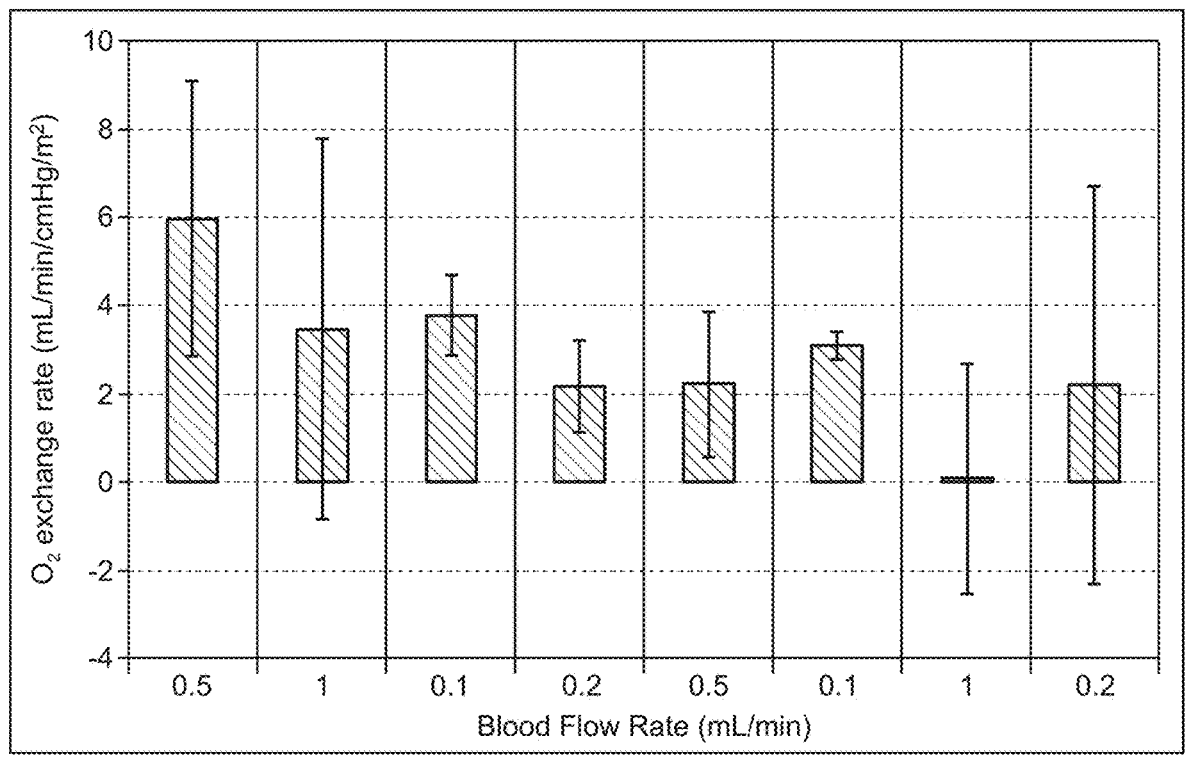

FIGS. 10A and 10B. (FIG. 10A) Ex vivo oxygen partial pressure in blood over time, with two cycles of randomized blood flow rates. Each blood flow rate was maintained for 20 minutes (FIG. 10B) Ex vivo oxygen exchange rates in chronological order.

Figure 11A:
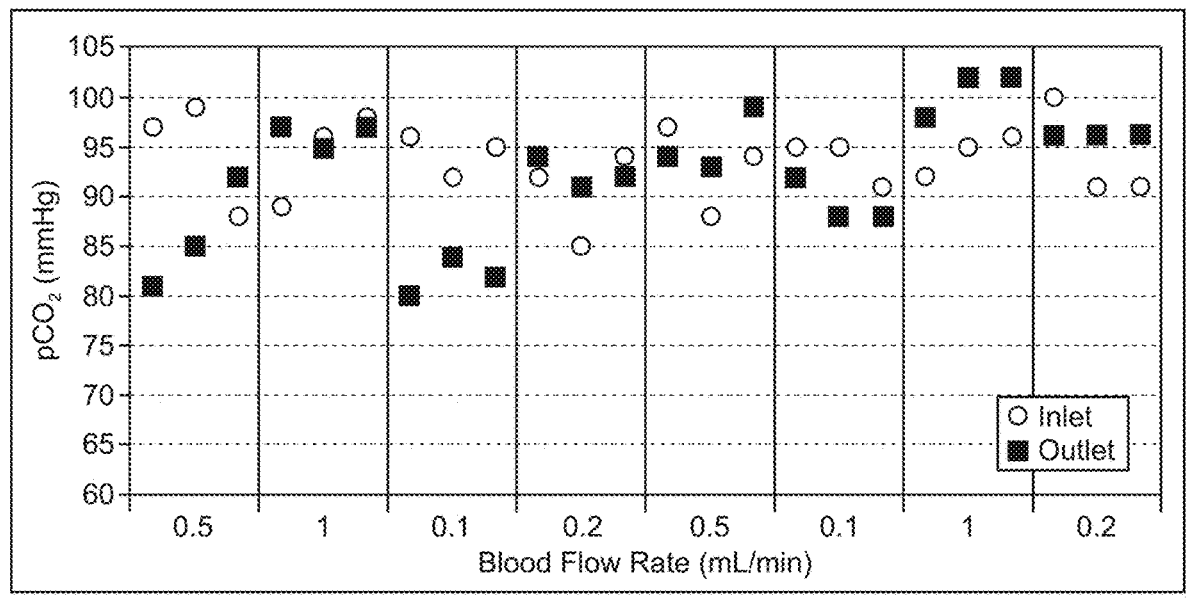
FIGS. 11A and 11B are a collection of graphs showing carbon dioxide partial pressure and carbon dioxide exchange rates, respectively, in blood flowing through a blood oxygenation device that includes a gas exchange composite membrane in ex vivo tests, according to embodiments of the present disclosure.
Figure 11B:
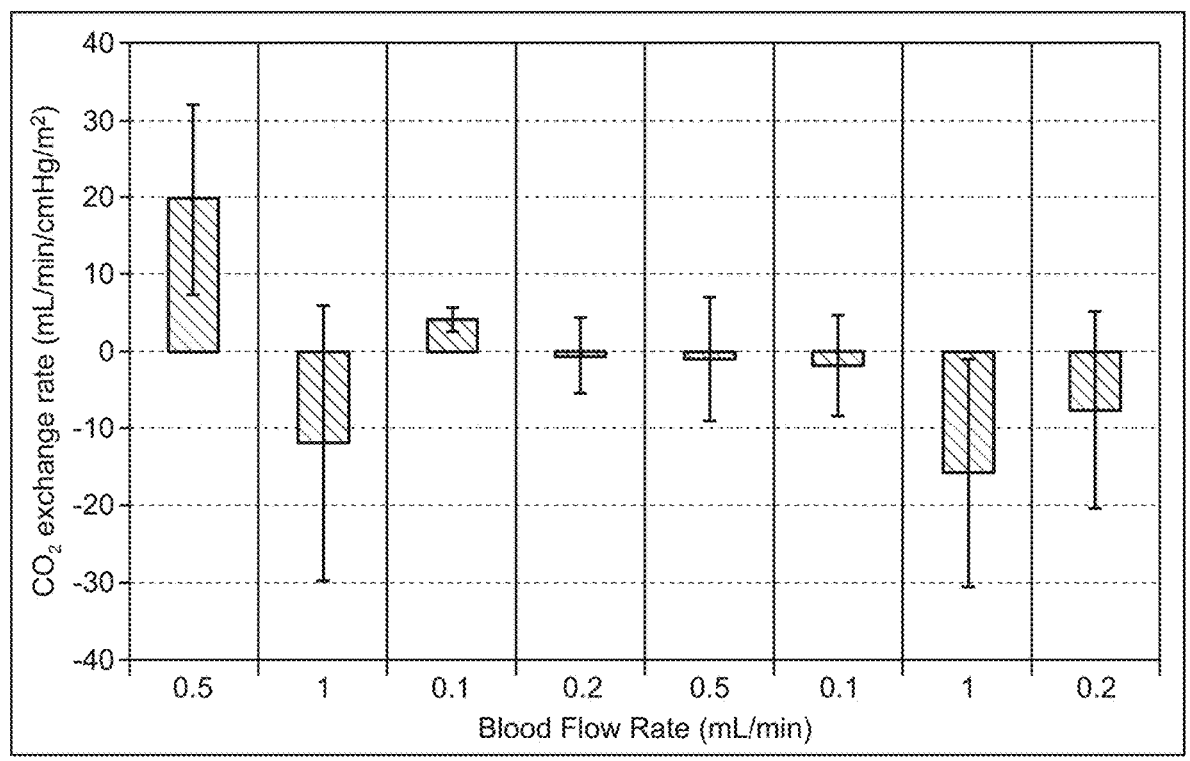

FIGS. 11A and 11B. (FIG. 11A) Ex vivo carbon dioxide partial pressure in blood. (FIG. 11B) Ex vivo carbon dioxide exchange rates in chronological order.

Ovine In Vivo Testing

The pressure drop across the device varied throughout the course of the test, ranging from 1.5 to 11.5 mmHg (FIG. 12); this variation was independent of flow rate, and generally increased over time. There was no gross coagulation of blood observed throughout the experiment, but the pattern of flow was dynamic. The animal remained hemodynamically stable for the duration.

Figure 12:
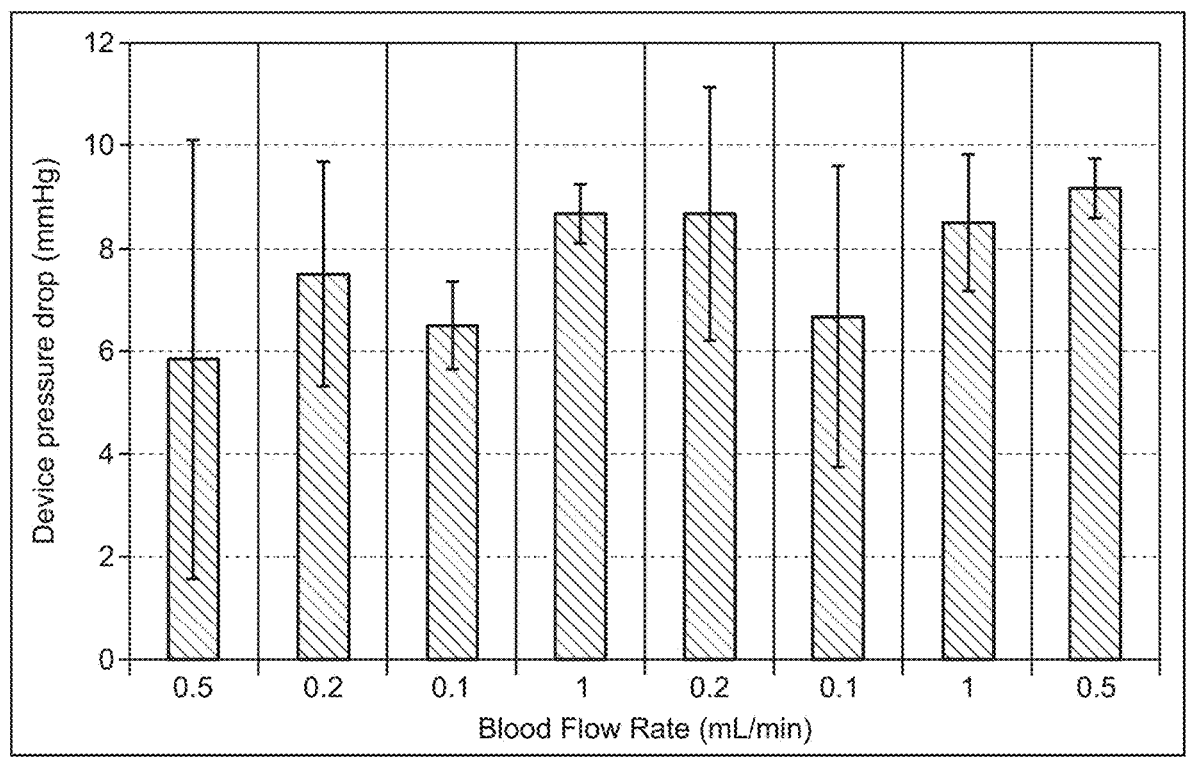
FIG. 12 is a graph showing pressure drop between an inlet and an outlet of blood flowing through a blood oxygenation device that includes a gas exchange composite membrane in in vivo tests, according to embodiments of the present disclosure.

FIG. 12. Pressure drop between oxygenator inlet and outlet (average±standard deviation) during in vivo tests. Blood flow rates were cycled twice in random order; results displayed in chronological order from left to right.

Figure 13A:
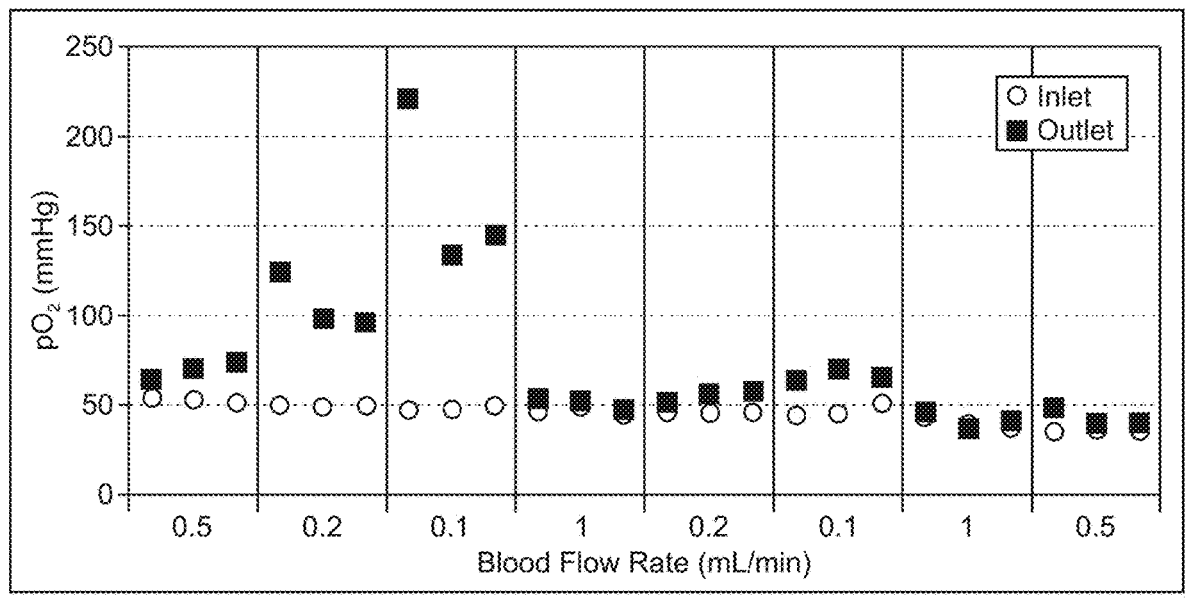
FIGS. 13A and 13B are a collection of graphs showing oxygen partial pressure and oxygen exchange rates, respectively, in blood flowing through a blood oxygenation device that includes a gas exchange composite membrane in in vivo tests, according to embodiments of the present disclosure.
Figure 13B:
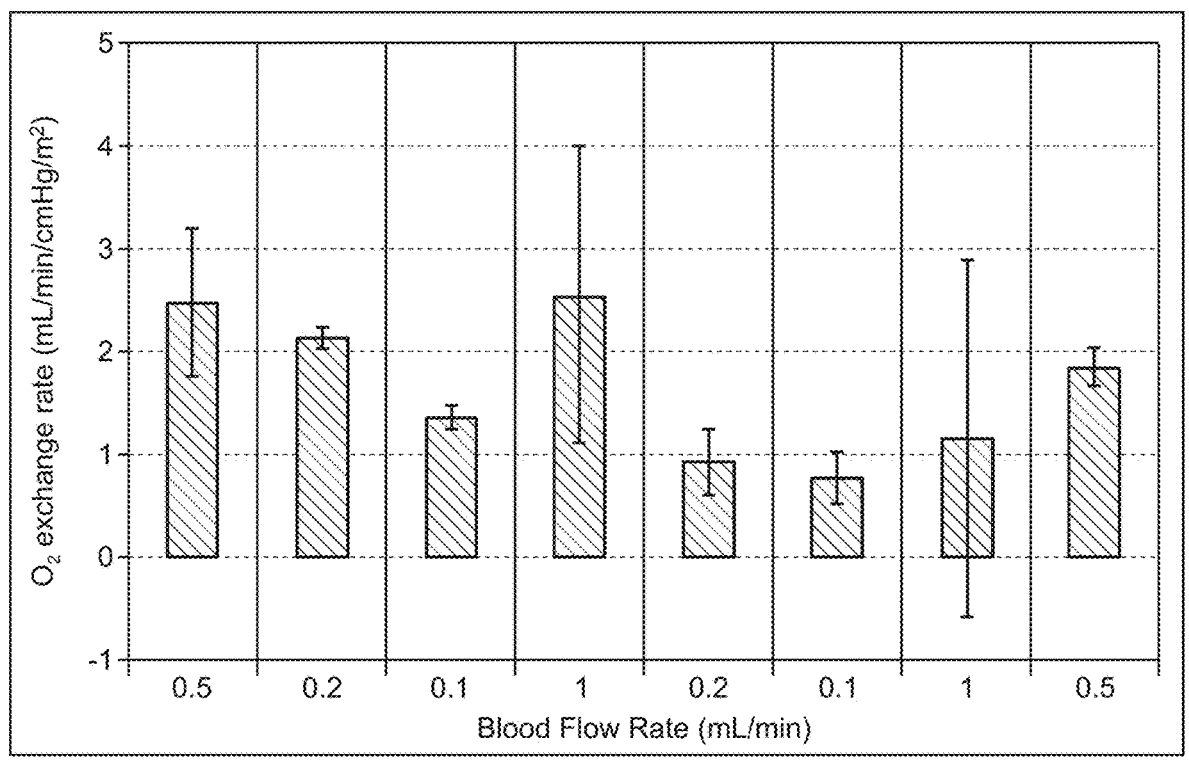
Figure 14A:
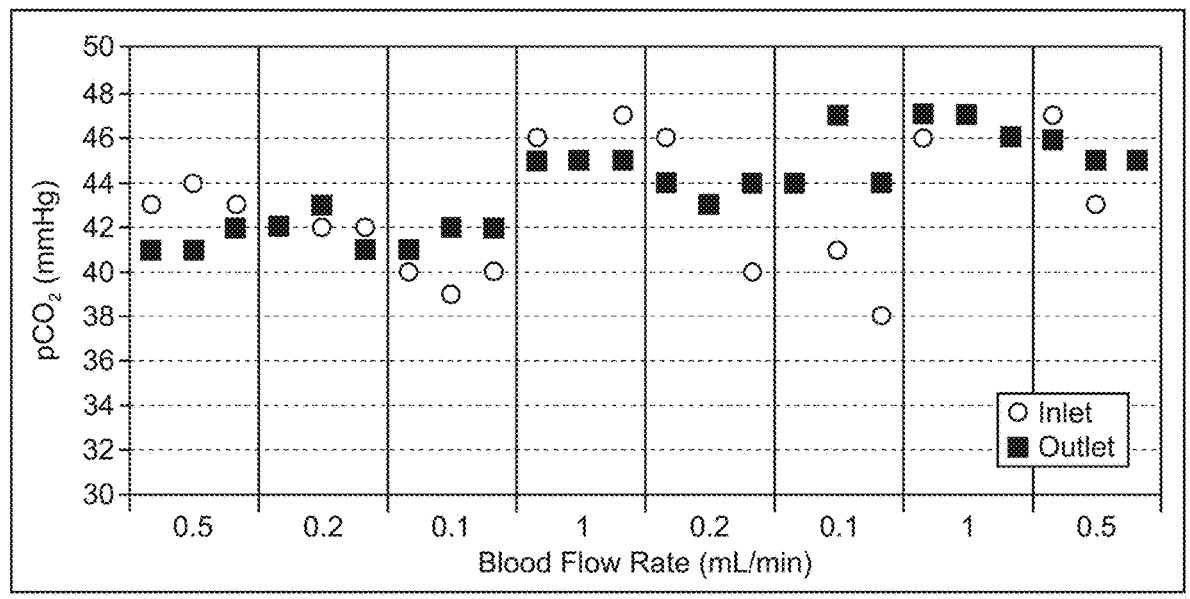
FIGS. 14A and 14B are a collection of graphs showing carbon dioxide partial pressure and carbon dioxide exchange rates, respectively, in blood flowing through a blood oxygenation device that includes a gas exchange composite membrane in in vivo tests, according to embodiments of the present disclosure.
Figure 14B:
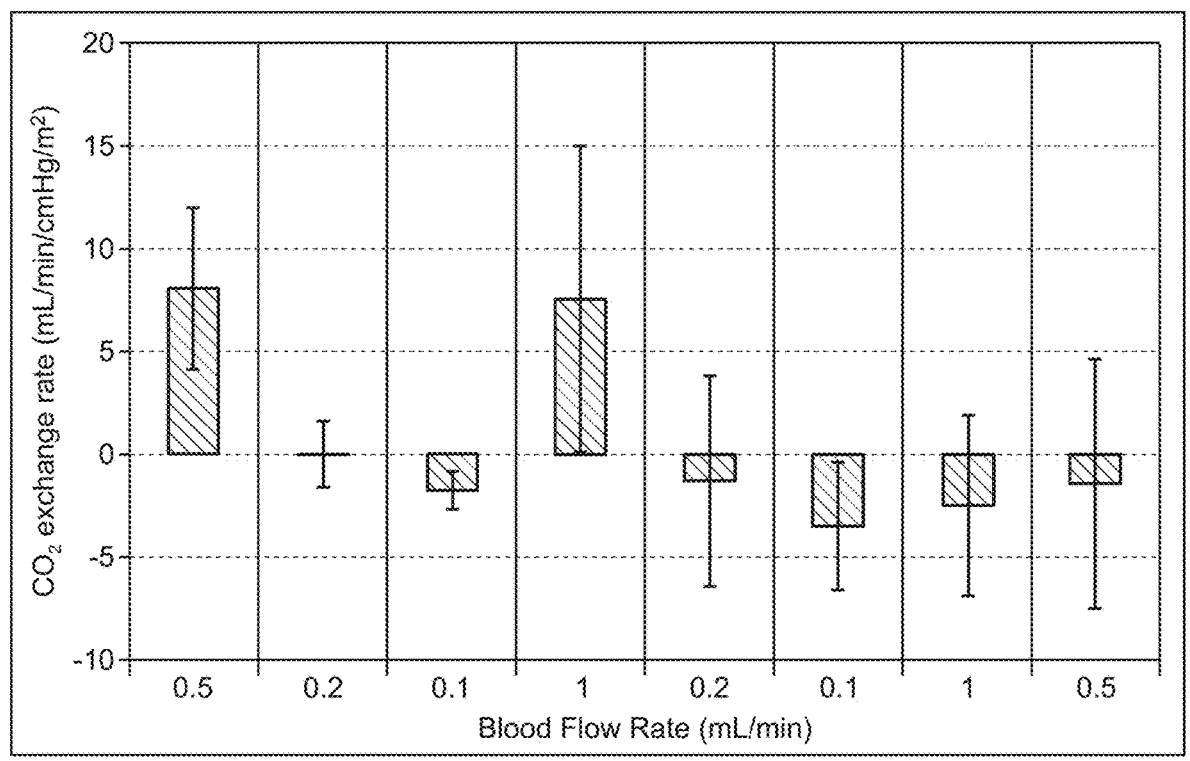

The inflow $pO_2$ declined over 3 hours from 54 mmHg to 37 mmHg (FIG. 13A). Oxygen permeability varied throughout the experiment with a general trend toward increased permeability at higher flow rates (FIG. 13B). The oxygen permeability over time remained fairly constant throughout the course of the experiment with the most notable finding being increased variability of permeability at the 1 mL/min flow rate. The inflow pH and $pCO_2$ remained stable at 7.35±0.01 and 43.2±2.7 mmHg, respectively (FIG. 14A). Similar to ex vivo results, there was no appreciable $CO_2$ exchange when averaged by flow rate (FIG. 14B). There was evidence of $CO_2$ exchange during the test at a blood flow rate of 0.5 mL/min, with permeability of 8.04±3.93 mL STP/min/cmHg/m². $CO_2$ exchange was negligible at all subsequent blood flow rates.

FIGS. 13A and 13B. (FIG. 13A) In vivo oxygen partial pressure in blood over time, with two cycles of randomized blood flow rates. Each blood flow rate was maintained for 20 minutes (FIG. 13B) In vivo oxygen exchange rates in chronological order.

FIGS. 14A and 14B. (FIG. 14A) In vivo carbon dioxide partial pressure in blood. (FIG. 14B) In vivo carbon dioxide exchange rates in chronological order.

Platelet and Blood Endothelial Cell Adhesion on Membranes

CD31-stained membranes showed minimal adhered cells after exposure to citrated blood ex vivo (FIG. 15A), with less than 0.05% occlusion. However, 12.5% of membrane area was occluded by cells and platelets after exposure to heparinized blood in vivo (FIG. 15B).

FIGS. 15A and B. (FIG. 15A) Epifluorescence image of CD31-labeled PDMS-SµM following conclusion of ex vivo blood oxygenation experiment; <0.05% membrane surface area is occluded by adhered platelets and other blood endothelial cells. (FIG. 15B) CD-31 labeling of adhered blood cells on PDMS-SµM following in vivo blood oxygenation experiment showed 12.5% occlusion of membrane surface area. Inset shows magnification of the indicated area.

Example 2: Planar Polydimethylsiloxane (PDMS)/Silicon Gas Exchange Membranes for Respiratory Support Applications Design In a simplified model of gas transport across a membrane shown in Eq. 1, gas flux (Q) across a membrane with a partial pressure difference between the sweep gas ($pO_{2,gas}$) and blood sides ($pO_{2,blood}$) is inversely proportional to the membrane diffusive conductance, or permeability, (S). A closer examination via Eq. 2 reveals that permeability is inversely proportional to membrane thickness (T). While material choice dictates the permittivity, K, for a given membrane of area, A, membrane thickness can be readily manipulated by adjusting fabrication parameters.

$$Q_{O_2} = (pO_{2,gas} - pO_{2,blood}) \cdot S \qquad (1)$$

$$S = \frac{A \cdot K}{T} \qquad (2)$$

Gas transport can therefore be enhanced by decreasing the membrane thickness or increasing the partial pressure of oxygen in the sweep gas to create a steeper concentration gradient. However, a thin membrane made of highly elastic PDMS can deform due to differences between the absolute pressures in the sweep gas and blood ($P_{gas}$ and $P_{blood}$, respectively), illustrated by Eq. 3, where u is deflection out of the membrane plane, E is membrane elastic modulus, and W, L, and T are width, length, and thickness of the membrane, respectively. This can lead to ballooning or collapse of the blood channel.

$$u \propto \frac{(P_{gas} - P_{blood}) \cdot W^5}{E \cdot T^3 \cdot L} \qquad (3)$$

Current microfluidic platforms incorporating thin PDMS membranes use narrow, high resistance blood channels to avoid large deformations induced by blood-gas pressure differences. To avoid these problems, a rigid, but highly porous, silicon micropore membrane was employed as a structural support that makes a minimal contribution to the total membrane diffusive resistance, while allowing the use of a micron-thin PDMS film in contact with blood.

Analytical modeling was used to predict the deformation of the PDMS membrane supported by SµMs, under a transmembrane pressure load of 77.6 cmHg, or approximately 150% of the expected pressure difference between the sweep gas and blood. Using the analytical solution for a simply-supported rectangular plate, Eq. 4 was used to determine the maximum deformation at the center of the PDMS membrane, $u_{max}$, where u is the Poisson ratio of the membrane material and the coefficient 0.15624 accounts for the ratio between the plate length and width. For ease of fabrication and subsequent material handling, a 4.5 µm thick PDMS film was chosen for evaluation.

$$u_{max} = 0.15624 \frac{(P_{gas} - P_{blood}) \cdot (1 - v^2) \cdot W^4}{E \cdot T^3} \qquad (4)$$

Modeling results indicated that a 4.5 µm thick PDMS film, suspended over 500 nm wide by 4 µm long rectangular pores in a SµM, would deform a maximum of 0.017 nm out of plane under a 77.6 cmHg uniform pressure load. A far more significant source of deformation is expected from the SµM window component, with a calculated maximum deformation under identical pressure loads of 351 nm. When used in an oxygenator with blood channel height on the order of 10-100 µm, this magnitude of deformation should have negligible effects on blood flow characteristics. For comparison, a 4.5 µm thick PDMS membrane spanning a 1 cm channel would experience large elastic deformation and collapse the channel under similar pressure loading.

Methods

Membrane Fabrication

Silicon micropore membranes (SµMs). SµMs were fabricated to produce wafer-scale arrays of 500 nm by 4 µm rectangular slit pores. First, a 1 µm thick thermally grown silicon dioxide layer was patterned with anchor regions to divide the wafer into 50 µm by 267 µm "window" sub regions. A 500 nm thick polysilicon film was then deposited and patterned via photolithography and reactive ion etching (RIE) to define evenly spaced parallel beams (FIG. 2, steps (1) and (2)). Lines and spaces were both 500 nm wide. The backside of the wafer was then patterned to define the same window dimensions using front-to-back alignment and deep reactive ion etching (DRIE), thereby exposing the backside of the polysilicon beams (FIG. 2, step (3)). Lastly, 49% hydrofluoric acid was used to remove the oxide etch-stop layer and open the membrane pores (FIG. 2, step (4)). For the purposes of this study, the wafers were diced to form 1 cm² membranes containing 1500 windows each, with a total of 3.12e6 pores per membrane. This granted an effective membrane area (die area occupied by windows) of 2.00e-5 m², with a window porosity of 40% and overall die porosity of 6.24%.

PDMS coating. SµMs were coated with polydimethylsiloxane (PDMS) via a liftoff process derived from Thangawng et al. ((Weinheim an Der Bergstrasse, Germany) 3, 132 (2007)) and Park et al. (Micromech Microeng 19, 065016 (2009)). A 15 µm thick layer of SU-8 photoresist (MicroChem Corp., Newton, Mass.) was spin-coated onto a silicon wafer and baked (FIG. 3C, step (1)). Sylgard 184

PDMS (Dow Corning, Midland, Mich.) was then mixed at a monomer to crosslinker ratio of 3:1 and spin-coated onto the photoresist (FIG. 3C, step (2)) at 4500 rpm for 2 min; the PDMS was heat-cured at 80° C. for 2 hr. The SμM was then bonded to the PDMS layer using oxygen plasma treatment at 150 W for 5 s (FIG. 3C, step (3)); a 2 μL drop of isopropyl alcohol was placed on the PDMS prior to contact with the silicon membrane to ensure a conformal bond as the alcohol evaporated. The complete asymmetric membrane unit was released from the silicon wafer by stripping the photoresist with acetone (FIG. 3C, step (4)).

Membrane Characterization

Membrane structure. SμM pore dimensions and membrane polysilicon thickness were measured using scanning electron microscopy (SEM). The PDMS film thickness was measured using both SEM and a contact profilometer (Ambios Technology, Inc., Santa Cruz, Calif.). Membrane mechanical robustness was experimentally verified by subjecting the complete PDMS-SμMs to leak testing using a bench top hydraulic permeability testing system, which is capable of measuring water flux per unit pressure on the order of nanoliters per minute in response to a transmembrane pressure gradient. Water was flowed in contact with the PDMS side of the membrane at a transmembrane pressure of 260 mmHg for 30 min. Membrane ruptures, or deformations greater than 1 μm out of plane, could be detected by outflow of water collected in a precision mass balance (Mettler Toledo, Columbus, Ohio).

Gas diffusion through membranes. The complete PDMS-SμMs were tested for gas permeability in a dry bench-top flow cell connected to a pressurized gas supply and a bubble flow meter (Sigma-Aldrich, St. Louis, Mo.). The pressurized gas, either oxygen or carbon dioxide, was applied to one side of the membrane to form a transmembrane partial pressure gradient between 700 and 1400 mmHg. Gas that diffused to the opposite side of the membrane was collected in the bubble flow meter, displacing a meniscus of detergent to measure the volume of gas transported across the membrane. By measuring the gas flux per unit pressure, gas permeability could be calculated for the PDMS-SμMs via Eq. 1. Membrane area used for this calculation was the total window area (2.00e-5 $m^2$).

Gas exchange with blood. The PDMS-SμMs were tested for gas permeability in a flowing blood environment using porcine whole blood, treated with 2 U/mL heparin. An acrylic flow cell, containing a 1 $cm^2$ PDMS-SμM (6.24e-6 $m^2$ effective gas exchange area), was used as a blood oxygenator and deoxygenator, with the PDMS side of the membrane in direct contact with blood while the silicon backside was exposed to a sweep gas, either oxygen or nitrogen, respectively (FIG. 6A). A total volume of 2 mL of blood was recirculated over the PDMS-SμM in a 50 μm high by 9 mm wide by 9 mm long channel at 2 mL/min. The blood flow rate was chosen to provide maximum shear without causing hemolysis, thereby reducing the boundary layer thickness at the membrane surface. The gas side of the membrane was first exposed to pure nitrogen at a partial pressure of 860 mmHg to deoxygenate the blood; the gas was then switched to pure oxygen to create a transmembrane partial pressure gradient of 1275 mmHg and drive oxygen diffusion into the blood. Oxygen partial pressure measurements were acquired at 1 Hz using a NeoFox inline optical oxygen sensor (Ocean Optics, Dunedin, Fla.), which was coated with a fluorophore coating that was quenched by oxygen. Total oxygen concentration was determined from the hemoglobin dissociation model developed by Margaria. The flow cell was then flushed with saline solution at 2 mL/min for 5 min, then disassembled and examined for gross clots.

FIG. 6A. Ex vivo blood oxygenation circuit with inline optical oxygen sensor.

Results

Membrane Structural Characterization

SμM dimensions were characterized using scanning electron microscopy (SEM) (FIG. 4B), confirming highly uniform pore dimensions of 3.55±0.03 μm long by 450±20 nm wide, with a polysilicon membrane thickness of 480±20 nm. The PDMS film thickness was measured by SEM to be 4.63±0.11 μm, which agreed closely with contact profilometry results.

FIG. 4B. Top view of SμM with dimensions of individual pores.

Hydraulic permeability testing of the complete PDMS-SμMs was carried out to detect membrane defects that would allow leaking of water under a transmembrane pressure gradient. Water flowed parallel to the PDMS side of the membrane at a transmembrane pressure of 260 mmHg for 30 min, with no water flux across the membrane detected. This confirmed that there was sufficient conformal bonding of the PDMS and SμM to prevent water or blood plasma from flowing around the PDMS and wetting the SμM pores.

Membrane Gas Permeability

Gas permeability of the PDMS-SμMs was first tested in a dry bench-top flow cell between air at ambient pressure and a pressurized pure gas source. The pressurized gas, either oxygen or carbon dioxide, was applied to one side of the membrane to form a transmembrane partial pressure gradient between 700 and 1400 mmHg. The volume of gas that diffused to the opposite side of the membrane was measured by a bubble flow meter. Measured gas flux per unit pressure was converted to gas permeability for the PDMS-SμMs via Eq. 1. Permeability to $O_2$ and $CO_2$ were found to be 9.86±1.92 and 57.10±1.43 mL $min^{-1}$ $m^{-2}$ $cmHg^{-1}$, respectively (FIG. 16).

Figure 16:
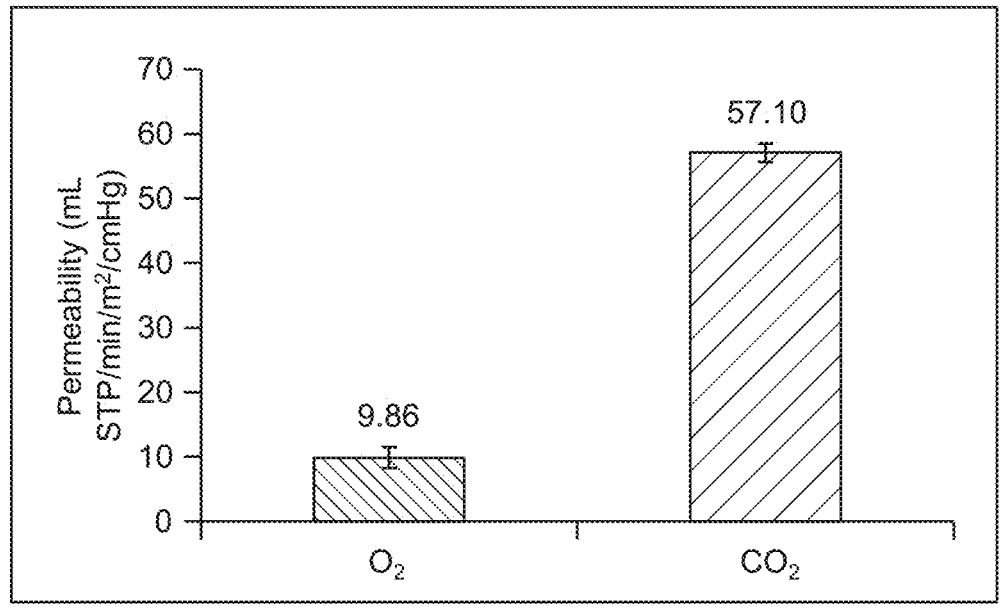
FIG. 16 is a graph showing gas permeability of a gas exchange composite membrane, according to embodiments of the present disclosure.

FIG. 16. Dry gas permeability of PDMS-SμMs.

Blood Oxygenation

Figure 17:
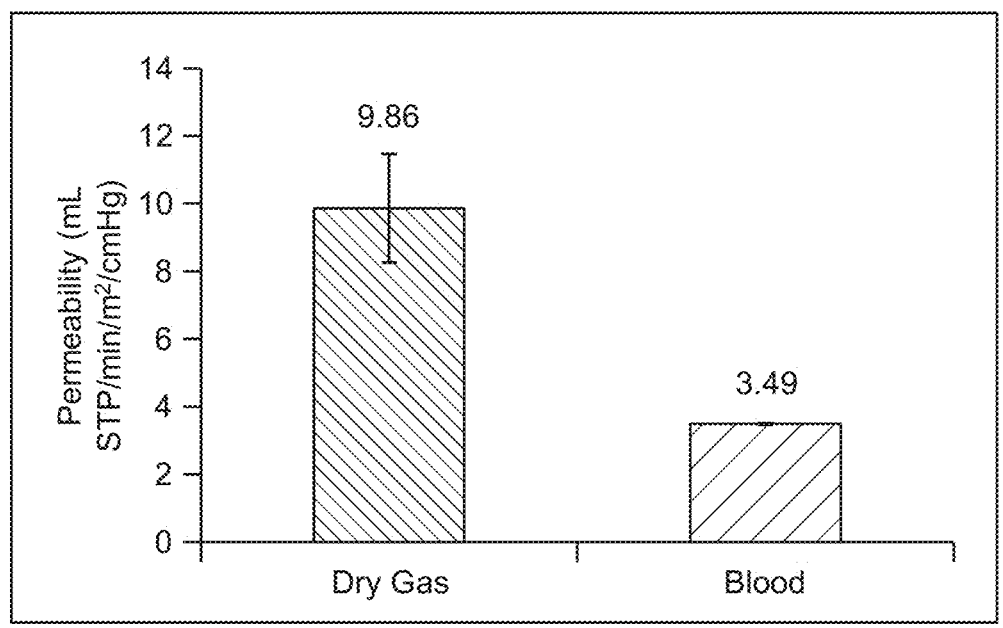
FIG. 17 is a graph showing oxygen transfer rate of a gas exchange composite membrane, according to embodiments of the present disclosure.

Heparinized porcine whole blood was flowed over the PDMS-SμM in a 50 μm high by 9 mm wide by 9 mm long channel at 2 mL/min. Repeated oxygen saturation and desaturation of blood was achieved with no gross clots in the flow cell or tubing for 3 hr, with a calculated oxygen permeability of 3.49±0.03 mL $min^{-1}$ $m^{-2}$ $cmHg^{-1}$ (FIG. 17). The oxygen transfer rate was consistent for the duration of the experiments, indicating negligible fouling of the membrane.

FIG. 17. Comparison of membrane gas permeability in contact with dry gas and blood.

Example 3: Development of a Novel Oxygenator Membrane—a Step Toward an Artificial Lung Methods Membrane Design and Fabrication Fabrication of a silicon micropore membrane (SμM). FIG. 2 illustrates a single membrane cross-section. Polysilicon was deposited and patterned on top of silicone dioxide film (FIG. 2, step (1)). The polysilicon was etched to define 0.5 μm by 4 μm rectangular pores (FIG. 2, step (2)). Then the backside bulk silicon was etched to open membrane window (FIG. 2, step (3)). Then, the sacrificial oxide layer was etched to open path between pores and back side of membrane FIG. 2, step (4).

Transfer of polydimethylsiloxane (PDMS) layer to SµMs. FIG. 3B illustrates a single membrane cross-section. A thick PDMS layer (~1 mm), polyvinyl alcohol (10% w/w) and thin layer of PDMS (~3 µm) were spun onto silanized silicon wafer and heat cured between each layer (FIG. 3B, step (1)). The thick PMDS-PVA-Thin PDMS layer was plasma-bonded to SµM (FIG. 3B, step (2)). The resulting construct was placed in water bath and the PVA layer dissolved (FIG. 3B, step (3)), yielding the complete PDMS-SµM.

Ex-Vivo Experimental Set-Up Using Whole Blood 6 cm×1 cm SµM-PDMS membranes were placed in flow chamber to achieve gas transport in the mini-oxygenator (FIG. 5).

In a closed loop system with a peristaltic pump at a constant flow rate, initially deoxygenated blood flowed across the surface of the SµM-PDMS membrane. A sweep gas of pure oxygen was kept at constant pressure on the backside of the membrane. Samples of the blood were taken throughout the experiment and changes in oxygen concentration over time were determined with a bench-top hemoximeter.

Results

Oxygen Saturation in Blood

Figure 18:
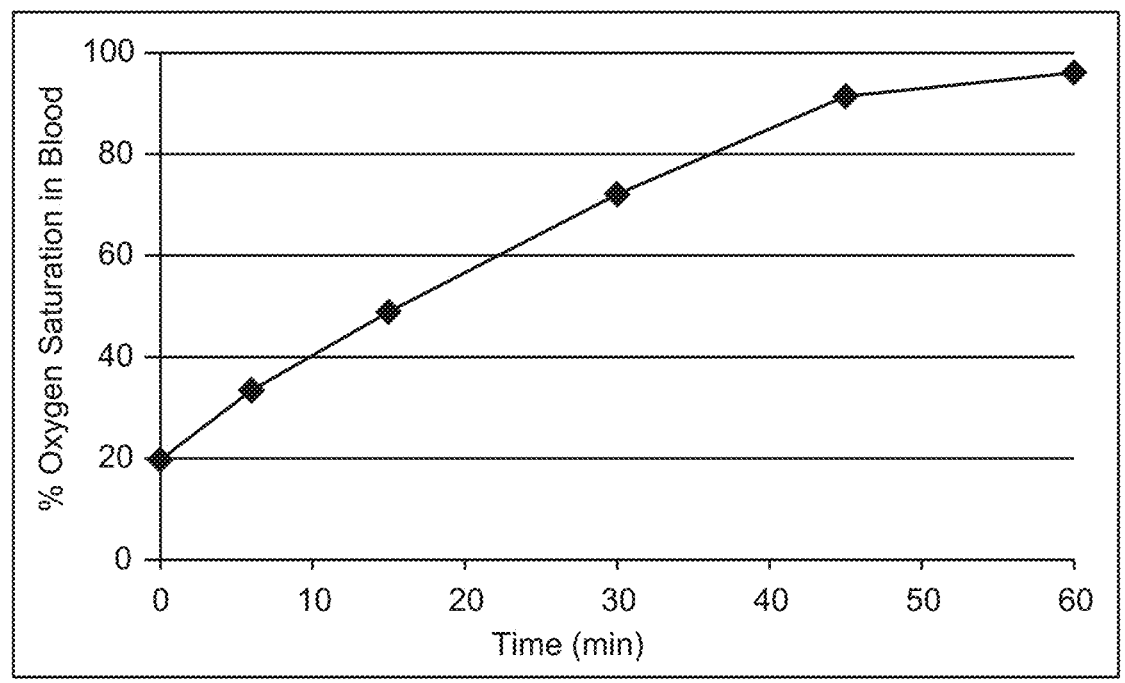
FIG. 18 is a graph showing blood oxygen saturation over time in a closed loop system when exposed to a gas exchange composite membrane, according to embodiments of the present disclosure.

The blood oxygen saturation increased over time when exposed to the oxygenator membrane (FIG. 18).

FIG. 18. $O_2$ Saturation vs Time in Blood. The blood volume in the closed loop system was 18.5 ml flowing at 10 ml/min with a channel height of 200 µm, and the sweep gas ($O_2$) pressure was kept constant around 0.53 cmHg.

Determining Oxygen Permeability

The following Equation 5 was used to calculate gas permeability (k):

$$k = \frac{\Delta C_{O_2} \times V_{blood}}{(p_{O_2,gas} - p_{O_2,blood}) \times t \times A_m},\quad (5)$$

where $C_{O2}$ is the concentration of $O_2$ (ml/l at STP), V is volume of blood (liters), $p_{O2}$ is the partial pressure of oxygen (cm Hg), t is time (min), $A_m$ is the area of the membrane oxygenator (m$^2$).

Figure 19:
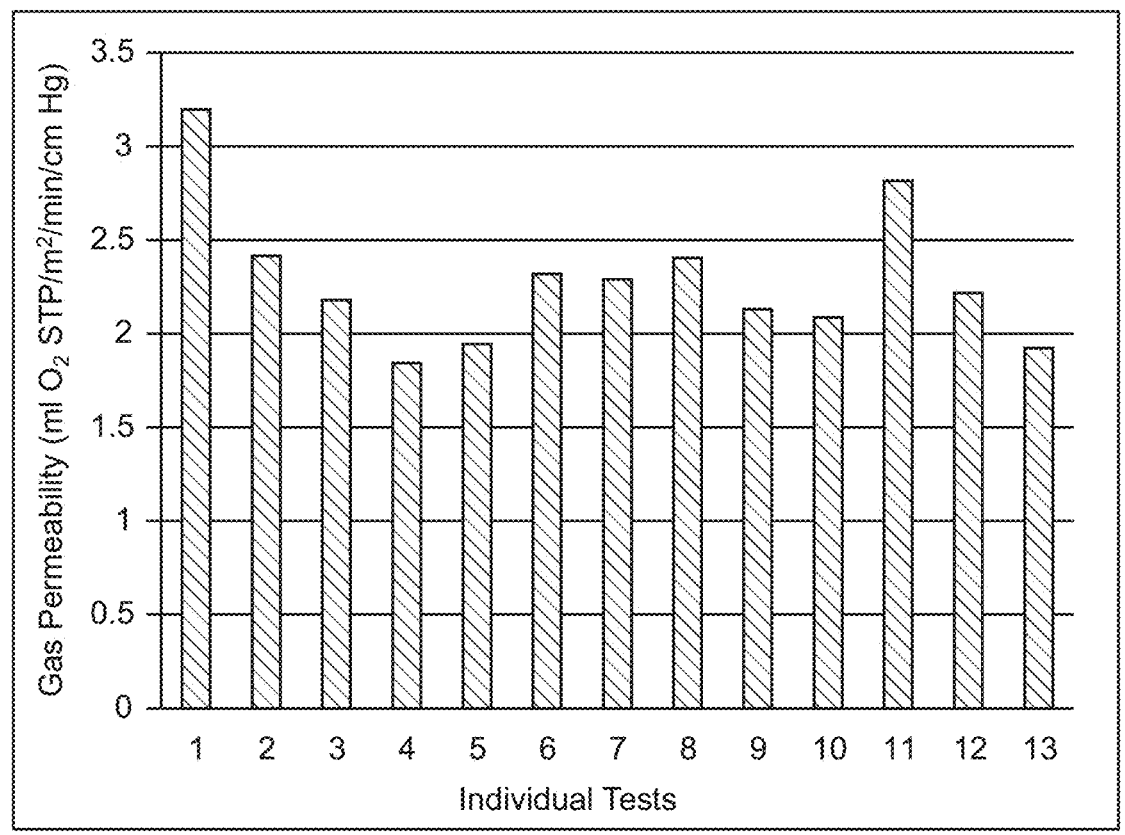
FIG. 19 is a graph showing oxygen permeability of a gas exchange composite membrane in ex vivo tests, according to embodiments of the present disclosure.

Average gas permeability was found to be 2.29 ml $O_2$ STP/min/m$^2$/cmHg with a standard deviation of 0.37 ml $O_2$ STP/min/m$^2$/cmHg (n=13) (FIG. 19). After testing membranes were inspected and found to have no visual defects.

FIG. 19. $O_2$ Permeability of SµM-PDMS Membranes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

What is claimed is:

1. A gas exchange composite membrane comprising:
   i) a non-porous, gas-permeable, polymeric membrane defining a first surface and a second surface opposite the first surface; and
   ii) a non-compliant, microporous membrane defining a third surface and a fourth surface opposite the third surface, wherein
   the microporous membrane comprises one or more gas diffusion windows, each comprising a network of struts defining walls of a plurality of micropores, each micropore extending from the third surface to the fourth surface; and
   the third surface is attached to the second surface,
   wherein the first surface of the polymeric membrane provides an antithrombotic surface for gas exchange over the one or more gas diffusion windows, between blood flowing along the first surface and a gas at the second surface.

2. The composite membrane of claim 1, wherein the first surface is substantially flat over the one or more gas diffusion windows.

3. The composite membrane of claim 1, wherein the composite membrane has an oxygen gas permeability against air of 5 mL STP/cmHg/m$^2$/min or more.

4. The composite membrane of claim 1, wherein the composite membrane has a carbon dioxide gas permeability against air of 20 mL STP/cmHg/m$^2$/min or more.

5. The composite membrane of claim 1, wherein the composite membrane has an oxygen gas transfer rate against blood of 0.5 mL STP/cmHg/m$^2$/min or more, at an average blood flow speed over the first surface in the range of about 1.0 to about 10 mm/sec.

6. The composite membrane of claim 1, wherein the composite membrane has a carbon dioxide transfer rate against blood of 2.0 mL STP/cmHg/m$^2$/min or more, at an average blood flow speed over the first surface in the range of about 1.0 to about 10.0 mm/sec.

7. The composite membrane of claim 1, wherein the polymeric membrane has an average thickness in the range of 0.01 to 100 µm.

8. The composite membrane of claim 1, wherein the microporous membrane has an average thickness in the range of 0.01 to 100 µm.

9. The composite membrane of claim 1, wherein each of the one or more gas diffusion windows has a porosity in the range of 1 to 90%.

10. The composite membrane of claim 1, wherein the one or more gas diffusion windows overlie an area in the range of 1.0 mm$^2$ to 1.0 m$^2$.

11. The composite membrane of claim 1, wherein a strut dividing adjacent micropores of the plurality of micropores have an average width in the range of 0.005 to 10.0 µm.

12. The composite membrane of claim 1, wherein the plurality of micropores is an array of micropores having substantially uniform dimensions.

13. The composite membrane of claim 12, wherein the array is a regular array of micropores.

14. The composite membrane of claim 1, wherein a micropore of the plurality of micropores has an average width in the range of 0.005 to 50 µm.

15. The composite membrane of claim 14, wherein the micropore has an average length in the range of 0.01 to 100 µm.

16. The composite membrane of claim 1, wherein the polymeric membrane is a polydimethylsiloxane (PDMS)-based polymeric membrane.

17. The composite membrane of claim 1, wherein the first surface is functionalized with an antifouling agent, an anticoagulant and/or an enzyme.

18. The composite membrane of claim 17, wherein the first surface is functionalized with polyethylene glycol, perfluorocarbon, heparin, polysulfobetaine methacrylate or carbonic anhydrase.

19. The composite membrane of claim 1, wherein the microporous membrane is a microporous polysilicon, silicon, silicon carbide, or silicon nitride membrane.

20. The composite membrane of claim 1, wherein the fourth surface comprises an anchoring strip that circumscribes each gas diffusion window, wherein the anchoring strip protrudes out relative to areas adjacent the anchoring strip on the fourth surface.

21. The composite membrane of claim 20, wherein the composite membrane further comprises a base substrate attached to the anchoring strip.

* * * * *